US009945735B2

(12) United States Patent
Georgeson et al.

(10) Patent No.: US 9,945,735 B2
(45) Date of Patent: Apr. 17, 2018

(54) SYSTEM AND METHOD TO MONITOR A THERMAL ENVIRONMENT OF A COMPOSITE STRUCTURE USING A THERMOCHROMATIC WITNESS ASSEMBLY

(71) Applicant: The Boeing Company, Chicago, IL (US)

(72) Inventors: Gary E. Georgeson, Tacoma, WA (US); Wesley L. Holman, Jr., Mill Creek, WA (US); Brandon P. Jamison, Charleston, SC (US); Randy J. Grove, Tukwila, WA (US)

(73) Assignee: The Boeing Company, Chicago, IL (US)

( * ) Notice: Subject to any disclaimer, the term of this patent is extended or adjusted under 35 U.S.C. 154(b) by 352 days.

(21) Appl. No.: 14/856,550

(22) Filed: Sep. 16, 2015

(65) Prior Publication Data

US 2016/0282198 A1 Sep. 29, 2016

Related U.S. Application Data

(63) Continuation-in-part of application No. 14/670,394, filed on Mar. 26, 2015.

(51) Int. Cl.
*G01K 11/12* (2006.01)
*B29C 35/02* (2006.01)
(Continued)

(52) U.S. Cl.
CPC .......... *G01K 11/12* (2013.01); *B29C 35/0288* (2013.01); *G01N 21/64* (2013.01);
(Continued)

(58) Field of Classification Search
CPC ...... B64F 5/0045; B64F 5/60; B29C 35/0288; B29C 73/34; G01K 11/12; G01K 11/125;
(Continued)

(56) References Cited

U.S. PATENT DOCUMENTS 3,744,295 A * 7/1973 Allinikov ............... G01N 21/91
252/960
5,662,712 A 9/1997 Pathak et al.
(Continued)

FOREIGN PATENT DOCUMENTS

EP 3026411 A1 6/2016

OTHER PUBLICATIONS

Extended European Search Report, dated Aug. 24, 2016, for corresponding EP application EP16152502.7-1703, Applicant The Boeing Company, 8 pages.
(Continued)

*Primary Examiner* — Lisa Caputo
*Assistant Examiner* — Philip Cotey

(57) ABSTRACT

There is provided a system, a method, and a thermochromatic witness assembly to monitor a thermal environment of a composite structure. The thermochromatic witness assembly has a polymeric material and one or more thermochromatic probes mixed into the polymeric material to form a thermochromatic probe mixture. The thermochromatic probe mixture is applied to a transparent polymeric film, or is formed into the transparent polymeric film with a pressure sensitive adhesive (PSA) applied thereto, thus forming the thermochromatic witness assembly in a form of a thermochromatic applique. The thermochromatic applique is configured to be applied directly and continuously to a surface of the composite structure. The thermochromatic applique is further configured to monitor the thermal environment of the composite structure by detecting one or more
(Continued)

temperatures and one or more times the surface of the composite structure is exposed to the thermal environment.

20 Claims, 20 Drawing Sheets

(51) Int. Cl.
    *G01N 21/64*     (2006.01)
    *G01N 21/71*     (2006.01)
    *B29C 73/34*     (2006.01)

(52) U.S. Cl.
    CPC .............. *G01N 21/71* (2013.01); *B29C 73/34* (2013.01); *G01N 2201/061* (2013.01)

(58) Field of Classification Search
    CPC ...... G01K 11/14; G01K 11/16; G01K 11/165; G01K 11/18; G01K 11/20; B29K 2020/16; G01N 21/61; G01N 21/71; G01N 2201/061
    See application file for complete search history.

(56) References Cited

U.S. PATENT DOCUMENTS

| | | | |
|---|---|---|---|
| 6,168,311 B1 | 1/2001 | Xiao et al. | |
| 6,652,778 B1* | 11/2003 | Twarowski | C09K 9/02 252/582 |
| 8,720,278 B1 | 5/2014 | Toivola et al. | |
| 9,085,052 B1 | 7/2015 | Georgeson et al. | |
| 2004/0147852 A1* | 7/2004 | Brister | A61B 1/00082 600/549 |
| 2006/0274812 A1* | 12/2006 | Safai | G01N 25/72 374/5 |
| 2008/0315163 A1* | 12/2008 | Schroer | G01K 11/12 252/586 |
| 2010/0136232 A1* | 6/2010 | Walker | B29C 35/049 427/248.1 |
| 2011/0132523 A1* | 6/2011 | Evens | B29C 73/10 156/94 |
| 2014/0273240 A1 | 9/2014 | Georgeson et al. | |
| 2014/0328369 A1* | 11/2014 | Flinn | G01N 33/442 374/57 |

OTHER PUBLICATIONS

Georgeson et al., "Monitoring Composite Manufacturing and Repair Processes Using Chromatic Films", U.S. Appl. No. 13/791,207, filed Mar. 8, 2013, 38 pages.

Georgeson et al., "Method and System for Detecting Exposure of Composites to High-Temperature", U.S. Appl. No. 13/840,980, filed Mar. 15, 2013, 24 pages.

Georgeson et al., "Witness Material and Method for Monitoring the Environmental History of an Object", U.S. Appl. No. 14/259,519, filed Apr. 23, 2014, 17 pages.

Georgeson et al., "Systems and Methods of Monitoring a Thermal Protection System", U.S. Appl. No. 14/337,622, filed Jul. 22, 2014, 20 pages.

Degaetano et al., "Chromatic Witness for Thermal Mapping and Certification of Heat Blankets", U.S. Appl. No. 14/555,364, filed Nov. 26, 2014, 16 pages.

Georgeson, Gary E., "Systems and Methods for Monitoring Temperatures of Batteries", U.S. Appl. No. 14/591,310, filed Jan. 7, 2015, 30 pages.

Safai et al., "Portable Device for Quantifying Thermochromatic Coating Signatures", U.S. Appl. No. 14/591,348, filed Jan. 7, 2015, 27 pages.

\* cited by examiner

SYSTEM AND METHOD TO MONITOR A THERMAL ENVIRONMENT OF A COMPOSITE STRUCTURE USING A THERMOCHROMATIC WITNESS ASSEMBLY

CROSS-REFERENCE TO RELATED APPLICATION

The present application is a continuation-in-part application of and claims priority to pending U.S. patent application Ser. No. 14/670,394, filed Mar. 26, 2015, entitled "System and Method to Map a Thermal Profile of a Composite Structure Using a Thermochromatic Witness Assembly", which is incorporated herein by reference in its entirety.

BACKGROUND

1) Field of the Disclosure

The disclosure relates generally to systems and methods for manufacturing or repairing composite structures, and more particularly, to systems and methods for mapping or monitoring the thermal profile of a composite structure during the curing process.

2) Description of Related Art

Composite structures may be used in a wide variety of applications, including in the manufacture of aircraft, spacecraft, rotorcraft, watercraft, automobiles, and other vehicles and structures, due to their high strength-to-weight ratios, corrosion resistance and other favorable properties. In particular, in aircraft construction, composite structures may be used to form the tail sections, wings, fuselage and other component parts of the aircraft.

During manufacturing of composite structures or parts, such as composite aircraft structures or parts, it is important to understand and control a thermal profile and a uniform temperature distribution over an entire area of the composite structure or part. If adjacent regions in the composite structure or part heat or cure at different rates, the resin properties may differ between those regions, potentially leading to built-in cure stresses, nonuniform consolidation and suboptimal properties.

Known systems and methods for monitoring the thermal profile of a composite structure or part during curing of early iterations of the composite structure or part and tooling exist. However, such known systems and methods may require significant effort, cost and time in order to optimize both the composite structure or part design and the tool design.

One such known method to monitor a thermal profile of a composite structure or part includes the use of thermocouples located on or implanted in the composite part or tool to monitor temperature. However, the thermocouples may only measure the temperature at specific point locations and may not measure out-of-range temperature information at other locations. Moreover, multiple thermocouples may be required on large or complex parts, and may result in increased time, labor and difficulty to install. In addition, the thermocouples typically remain on the composite structure or part during manufacturing and are removed after manufacturing. This may produce mark-off, such as resin pockets, resin "bumps", wrinkles, or geometry issues, on the resulting manufactured structure or part. Further, the thermocouples may have less than desired reliability, if the thermocouples do not work properly or if they experience wire breakage.

Accordingly, there is a need in the art for an improved system and method for mapping or monitoring a thermal profile of a composite structure or part during the curing process in the manufacture or repair of the composite structure or part, that provide advantages over known systems and methods.

In addition, a Thermal Protection System (TPS), such as insulation blankets, may be used to insulate propulsion system structures or parts, such as the inner walls of an engine cowling or cover, that may be exposed to high temperatures and high heat (e.g., greater than 250° F. (degrees Fahrenheit)). When high heat penetrates the TPS, the TPS may not function properly, or as designed, and may result in service issues.

To monitor the TPS, known systems and methods exist that use multiple thermocouples mounted at various locations on a composite structure or part to measure temperatures at the various locations during flight testing, ground testing, and/or in-service monitoring. However, with such known systems and methods, the thermocouples may only measure the temperatures at specific point locations and may not measure out-of-range temperature information at other locations. Coverage depends upon how many thermocouples are used, and it may be difficult or impractical to provide full coverage temperature monitoring and thermal mapping using only thermocouples. For example, positioning of multiple thermocouples on large or complex structures or parts may result in increased time and labor to install. Moreover, removal of the thermocouples may produce mark-off, such as resin pockets, resin "bumps", wrinkles, or geometry issues, on the resulting manufactured structure or part.

Accordingly, there is a need in the art for an improved system and method for monitoring a thermal environment of a composite structure or part during flight testing, ground testing, and/or in-service monitoring, that provide advantages over known systems and methods.

SUMMARY

Example implementations of this disclosure provide an improved system and method to map or monitor a thermal profile of a composite structure or part during the curing process in the manufacture or repair of the composite structure or part. As discussed in the below detailed description, embodiments of the improved method and system may provide significant advantages over existing systems and methods for mapping the thermal history or profile of composite structures or parts.

In addition, example implementations of this disclosure provide an improved system and method to monitor a thermal environment of a composite structure or part during flight testing, ground testing, and/or in-service monitoring. As discussed in the below detailed description, embodiments of the improved method and system may provide significant advantages over existing systems and methods for monitoring the thermal environment of composite structures or parts.

In one embodiment there is provided a system to map a thermal profile of a composite structure during curing in at least one of manufacture of the composite structure, or repair of the composite structure. The system comprises a thermochromatic witness assembly. The thermochromatic witness assembly comprises a first series of probes comprising a thermochromatic material either applied to a composite lay-up, or applied to a removable material adjacent the composite lay-up.

The system further comprises a process assembly with a heat source configured to cure the thermochromatic witness assembly to form the composite structure. The system further comprises a light source configured to activate the thermochromatic material of the first series of probes to prompt an onset of color changes in the thermochromatic material to determine one or more maximum temperatures of the composite structure, in order to map the thermal profile of the composite structure during curing in at least one of manufacture of the composite structure, or repair of the composite structure.

In another embodiment there is provided a method to map a thermal profile of a composite structure during curing in at least one of manufacture of the composite structure, or repair of the composite structure manufacture. The method comprises the step of applying a first series of probes comprising a thermochromatic material either to a composite lay-up on a tool, or to a removable material adjacent the composite lay-up, to form a thermochromatic witness assembly.

The method further comprises the step of curing with heat the thermochromatic witness assembly to form the composite structure. The method further comprises the step of activating the thermochromatic material of the first series of probes with a light source to prompt an onset of color changes in the thermochromatic material to determine one or more maximum temperatures of the composite structure, in order to map the thermal profile of the composite structure during curing in at least one of manufacture of the composite structure, or repair of the composite structure.

In another embodiment there is provided a method to map a thermal profile of an aircraft composite part during curing in at least one of manufacture of the aircraft composite part, or repair of the aircraft composite part. The method comprises the step of verifying a tool thermal profile of a tool configured for receiving a composite lay-up or configured for receiving the composite lay-up with a removable material adjacent the composite lay-up.

The method further comprises the step of applying a first series of probes comprising a thermochromatic material and a second series of probes comprising the thermochromatic material either to the composite lay-up on the tool, or to the removable material adjacent the composite lay-up, to form a thermochromatic witness assembly. The method further comprises the step of processing the thermochromatic witness assembly, including using heat to cure the thermochromatic witness assembly, to form the aircraft composite part.

The method further comprises the step of activating the thermochromatic material of the first series of probes with an ultraviolet (UV) light source to prompt an onset of color changes in the thermochromatic material of the first series of probes to determine one or more maximum temperatures of the composite part, in order to map the thermal profile of the aircraft composite part during curing in at least one of manufacture of the aircraft composite part, or repair of the aircraft composite part. The method further comprises the step of activating the thermochromatic material of the second series of probes with the light source, the second series of probes configured to provide a time-temperature profile of the aircraft composite part. The method further comprises the step of recording with a camera one or more images of the thermochromatic material of the first series of probes and the second series of probes. The method further comprises the step of removing the removable material, if the removable material is present in the thermochromatic witness assembly.

In another embodiment there is provided a thermochromatic witness assembly to monitor a thermal environment of a composite structure. The thermochromatic witness assembly comprises a polymeric material. The thermochromatic witness assembly further comprises one or more thermochromatic probes mixed into the polymeric material to form a thermochromatic probe mixture.

The thermochromatic probe mixture is applied to a transparent polymeric film, or is formed into the transparent polymeric film with a pressure sensitive adhesive (PSA) applied thereto, thus forming the thermochromatic witness assembly in a form of a thermochromatic applique. The thermochromatic applique is configured to be applied directly and continuously to a surface of the composite structure. The thermochromatic applique is further configured to monitor the thermal environment of the composite structure by detecting one or more temperatures and one or more times the surface of the composite structure is exposed to the thermal environment.

In another embodiment there is provided a system to monitor a thermal environment of a composite structure to facilitate optimization of a design of the composite structure. The system comprises a thermochromatic witness assembly comprising a thermochromatic applique or a thermochromatic paint, each comprising a plurality of thermochromatic probes mixed into a polymeric material.

The thermochromatic witness assembly is applied to a surface of the composite structure to obtain a covered surface. The covered surface is exposed to thermal conditions during one or more tests performed in the thermal environment, to obtain an exposed surface having one or more maximum temperature locations.

The system further comprises a light source configured to fluoresce the plurality of thermochromatic probes of the covered surface and the exposed surface. The plurality of thermochromatic probes is selected to sense one or more temperatures in the thermal environment. The system further comprises an imaging device configured to image and record one or more images of the covered surface and the exposed surface, after application of the light source.

The system further comprises a baseline map comprising one or more baseline colors and one or more baseline intensities. The baseline map is obtained by applying the light source to the covered surface and imaging the covered surface.

The system further comprises one or more thermal maps, each comprising one or more exposed colors and one or more exposed intensities. The one or more thermal maps are each obtained by applying the light source to the exposed surface and imaging the exposed surface.

The system further comprises a time-temperature history of the composite structure. The time-temperature history is obtained by comparing color changes between the one or more exposed colors and the one or more baseline colors, and by comparing intensity changes between the one or more exposed intensities and the one or more baseline intensities.

In another embodiment, there is provided a method to monitor a thermal environment of a composite structure to facilitate optimization of a design of the composite structure. The method comprises the step of applying a thermochromatic witness assembly, comprising a plurality of thermochromatic probes mixed into a polymeric material, to a surface of the composite structure, to obtain a covered surface. The composite structure is configured to undergo one or more tests performed in the thermal environment.

The method further comprises the step of applying a light source to the covered surface to fluoresce the plurality of thermochromatic probes, to obtain a baseline map comprising one or more baseline colors and one or more baseline intensities. The method further comprises the step of imaging and recording with an imaging device, the one or more baseline colors and the one or more baseline intensities of the baseline map.

The method further comprises the step of exposing the covered surface to thermal conditions in the thermal environment during the one or more tests, to obtain an exposed surface having one or more maximum temperature locations, and monitoring the thermal environment with the thermochromatic witness assembly. The method further comprises the step of applying the light source to the exposed surface to fluoresce the plurality of exposed thermochromatic probes, to obtain one or more thermal maps each comprising one or more exposed colors and one or more exposed intensities.

The method further comprises the step of imaging and recording with the imaging device, one or more exposed colors and one or more exposed intensities of the one or more thermal maps. The method further comprises the step of comparing color changes between the one or more exposed colors and the one or more baseline colors, and comparing intensity changes between the one or more exposed intensities and the one or more baseline intensities, to obtain a time-temperature history of the composite structure.

The method further comprises the step of using the time-temperature history to facilitate optimization of the design of the composite structure.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

The figures shown in this disclosure represent various aspects of the embodiments presented, and only differences will be discussed in detail.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and fully convey the scope of the disclosure to those skilled in the art.

Figure 1:
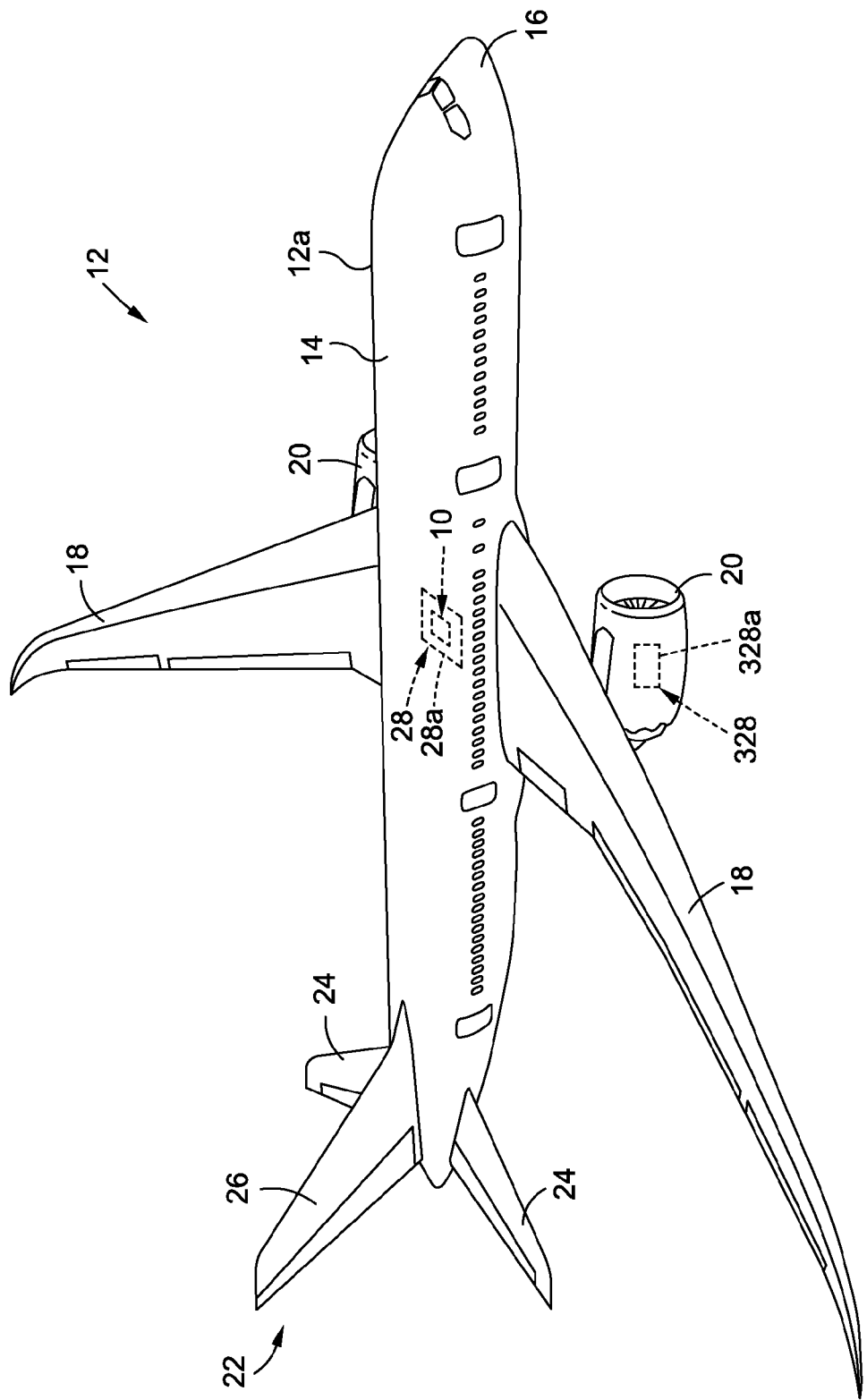
FIG. 1 is a diagrammatic representation of a perspective view of an air vehicle that may incorporate one or more composite structures that may be thermally mapped with an embodiment of a system and a method of the disclosure.

Now referring to the Figures, FIG. 1 is a diagrammatic representation of a perspective view of an air vehicle 12, such as in the form of aircraft 12a, that may incorporate one or more composite structures 28 that may be thermally mapped with an embodiment of a system 10 (see FIG. 4) and a method 200 (see FIG. 9) or a method 250 (see FIG. 10) of the disclosure. As further shown in FIG. 1, the air vehicle 12, such as in the form of aircraft 12a, comprises a fuselage 14, a nose 16, wings 18, engines 20, and an empennage 22 comprising horizontal stabilizers 24 and a vertical stabilizer 26.

As further shown in FIG. 1, the air vehicle 12, such as in the form of aircraft 12a, comprises one or more composite structures 28, such as in the form of an aircraft composite part 28a, for which a thermal profile 62 (see FIG. 4) may be mapped or monitored using the system 10 (see FIG. 4), the method 200 (see FIG. 9), and the method 250 (see FIG. 10), of the disclosure. In an exemplary embodiment, the composite structure 28 (see FIG. 1) comprises the aircraft composite part 28a (see FIG. 1) on the air vehicle 12 (see FIG. 1), such as aircraft 12a (see FIG. 1). In other embodiments (not shown), the composite structure 28 (see FIG. 1) may comprise a rotorcraft composite structure on a rotorcraft, a watercraft composite structure on a watercraft, or another suitable composite structure 28.

Figure 2:
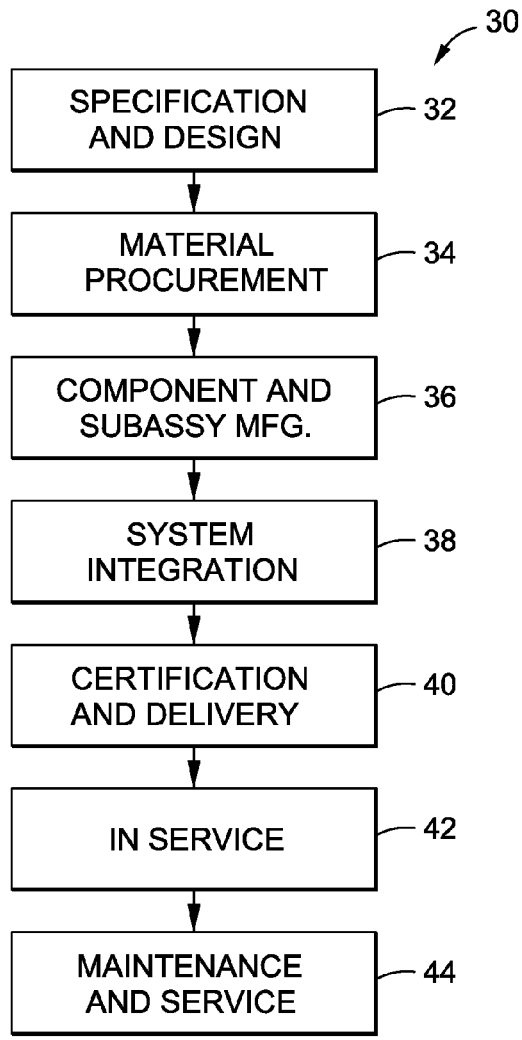
FIG. 2 is a flow diagram of an aircraft manufacturing and service method.
Figure 3:
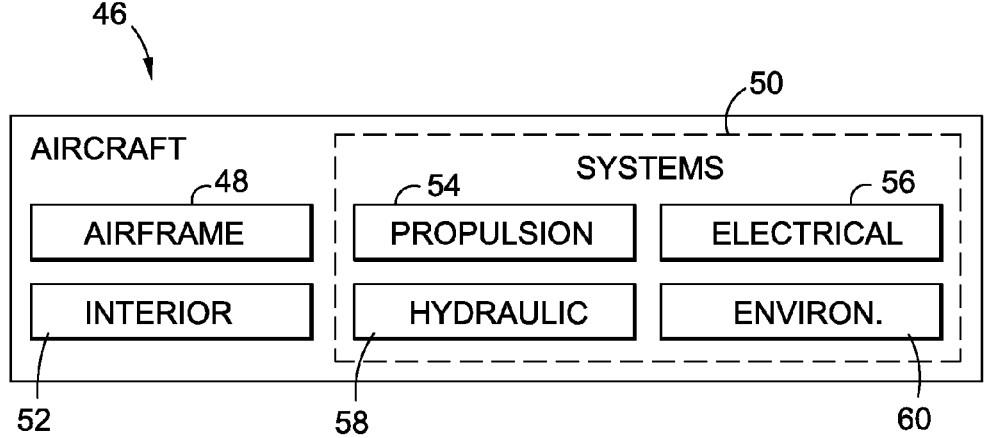
FIG. 3 is an illustration of a block diagram of an aircraft.

FIG. 2 is a flow diagram of an embodiment of an aircraft manufacturing and service method 30. FIG. 3 is an illustration of a functional block diagram of an embodiment of an aircraft 46. Referring to FIGS. 2-3, embodiments of the disclosure may be described in the context of the aircraft manufacturing and service method 30, as shown in FIG. 2, and the aircraft 46, as shown in FIG. 3. During preproduction, the exemplary aircraft manufacturing and service method 30 (see FIG. 2) may include specification and design 32 (see FIG. 2) of the aircraft 46 (see FIG. 3) and material procurement 34 (see FIG. 2). During manufacturing, component and subassembly manufacturing 36 (see FIG. 2) and system integration 38 (see FIG. 2) of the aircraft 46 (see FIG. 3) takes place. Thereafter, the aircraft 46 (see FIG. 3) may go through certification and delivery 40 (see FIG. 2) in order to be placed in service 42 (see FIG. 2). While in service 42 (see FIG. 2) by a customer, the aircraft 46 (see FIG. 3) may be scheduled for routine maintenance and service 44 (see FIG. 2), which may also include modification, reconfiguration, refurbishment, and other suitable services.

Each of the processes of the aircraft manufacturing and service method 30 (see FIG. 2) may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may include an airline, leasing company, military entity, service organization, and other suitable operators.

As shown in FIG. 3, the aircraft 46 produced by the exemplary aircraft manufacturing and service method 30 may include an airframe 48 with a plurality of systems 50 and an interior 52. As further shown in FIG. 3, examples of the systems 50 may include one or more of a propulsion system 54, an electrical system 56, a hydraulic system 58, and an environmental system 60. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 30 (see FIG. 2). For example, components or subassemblies corresponding to component and subassembly manufacturing 36 (see FIG. 2) may be fabricated or manufactured in a manner similar to components or subassemblies produced while the aircraft 46 (see FIG. 3) is in service 42 (see FIG. 2). Also, one or more apparatus embodiments, method embodiments, or a combination thereof, may be utilized during component and subassembly manufacturing 36 (see FIG. 2) and system integration 38 (see FIG. 2), for example, by substantially expediting assembly of or reducing the cost of the aircraft 46 (see FIG. 3). Similarly, one or more of apparatus embodiments, method embodiments, or a combination thereof, may be utilized while the aircraft 46 (see FIG. 3) is in service 42 (see FIG. 2), for example and without limitation, to maintenance and service 44 (see FIG. 2).

Figure 4:
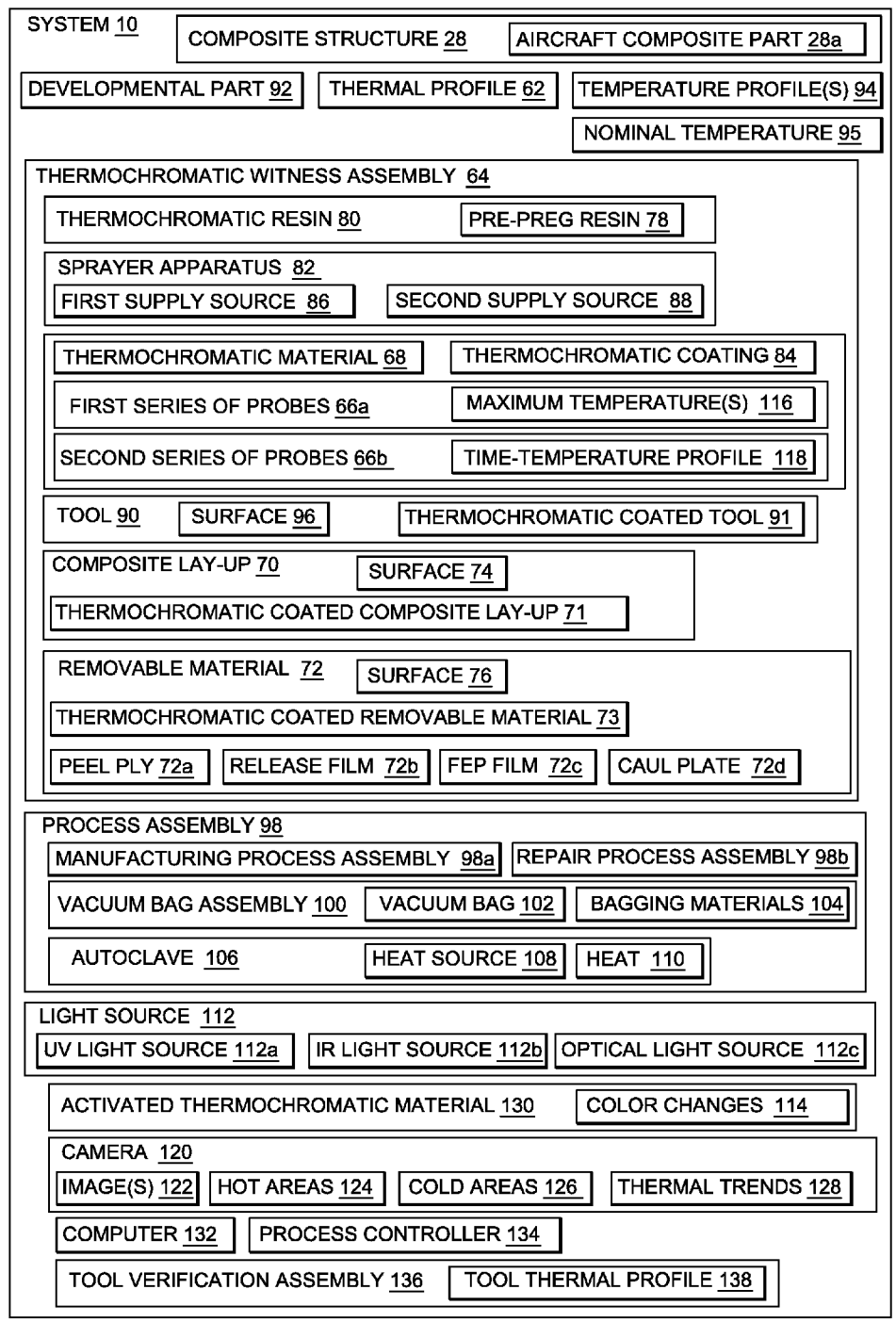
FIG. 4 is an illustration of a functional box diagram showing an embodiment of the system of the disclosure.

Referring to FIG. 4, in an embodiment of the disclosure, there is provided a system 10 to map a thermal profile 62 of a composite structure 28 during curing in at least one of manufacture of the composite structure, or repair of the composite structure. "At least one of" may mean only manufacture of the composite structure 28, or only repair of the composite structure 28, or a combination of manufacture of the composite structure 28 and repair of the composite structure 28. FIG. 4 is an illustration of a functional box diagram showing an embodiment of the system 10 of the disclosure. As shown in FIG. 4, the system 10 comprises a composite structure 28, such as an aircraft composite part 28*a*. Although a composite structure 28 (see FIG. 4) is preferable, metal structures or a combination of composite and metal structures may also be used.

As shown in FIG. 4, the system 10 further comprises a thermochromatic witness assembly 64. The thermochromatic witness assembly 64 (see FIG. 4) comprises a first series of probes 66*a* (see FIG. 4) comprising a thermochromatic material 68 (see FIG. 4). The thermochromatic witness assembly 64 (see FIG. 4) may further comprise a second series of probes 66*b* (see FIG. 4) comprising the thermochromatic material 68 (see FIG. 4). The thermochromatic witness assembly 64 (see FIG. 4) may further comprise, as needed, additional series of probes comprising the thermochromatic material 68 (see FIG. 4).

The thermochromatic material 68 (see FIG. 4) may comprise thermochromatic probes or dyes tailored to activate at specific thermal or time-temperature ranges. When the thermochromatic material 68 (see FIG. 4) is activated by exposure to the temperatures to which it has been tailored, the probe or dye undergoes fluorescent shifts. When illuminated by a light source 112 (see FIG. 4), discussed in further detail below, of a suitable wavelength, the fluorescent shifts in the thermochromatic material 68 (see FIG. 4) become visible, manifesting themselves as color change(s) 114 (see FIG. 4) or color intensity.

In one embodiment, as shown in FIG. 4, the thermochromatic witness assembly 64 comprises the first series of probes 66*a*, or alternatively, the first series of probes 66*a* and the second series of probes 66*b*, applied to a composite lay-up 70, and preferably to a surface 74 of the composite lay-up 70. The composite lay-up 70 may preferably comprise uncured composite plies 69, or other suitable composite plies, that are preferably cut and laid up via a known lay-up process and using a known lay-up apparatus. The lay-up apparatus may be an automated lay-up apparatus or a manual lay-up apparatus.

In another embodiment, as shown in FIG. 4, the thermochromatic witness assembly 64 comprises the first series of probes 66*a*, or alternatively, the first series of probes 66*a* and the second series of probes 66*b*, applied to the removable material 72 that is positioned adjacent to the composite lay-up 70, and preferably to a surface 76 of the removable material 72. The removable material 72 (see FIG. 4) preferably comprises at least one of a peel ply 72*a* (see FIG. 4), a release film 72*b* (see FIG. 4), a fluorinated ethylene propylene (FEP) film 72*c* (see FIG. 4), a caul plate 72*d* (see FIG. 4), or another suitable removable material 72. "At least one of" may mean either only a peel ply 72*a* (see FIG. 4), only a release film 72*b* (see FIG. 4), only a fluorinated ethylene propylene (FEP) film 72*c* (see FIG. 4), only a caul plate 72*d* (see FIG. 4), or only another suitable removable material 72, or any combination of a peel ply 72*a* (see FIG. 4), a release film 72*b* (see FIG. 4), a fluorinated ethylene propylene (FEP) film 72*c* (see FIG. 4), a caul plate 72*d* (see FIG. 4), and another suitable removable material 72.

The peel ply 72*a* (see FIG. 4) may comprise a woven fabric made of nylon, polyester fibers, or other suitable woven fabric materials. The peel ply 72*a* (see FIG. 4) is preferably peeled from the surface of the composite structure 28 (see FIGS. 1, 4) and removed following curing, and may be used to give texture to the surface of the composite structure 28 (see FIGS. 1, 4) or protect the surface of the composite structure 28 (see FIGS. 1, 4) from contaminants following a vacuum bagging process.

The release film 72*b* (see FIG. 4) may comprise a thin, elastic plastic film that facilitates pulling various bagging materials 104 (see FIG. 4) from a vacuum bag assembly 100 (see FIG. 4) off the composite structure 28 (see FIG. 1). The selection of the release film 72*b* (see FIG. 4) may be determined based on the resin system being used with a composite lay-up 70 (see FIG. 4), the temperature and pressure of the cure cycle, the shape of the composite structure 28 (see FIG. 4) to be cured and the amount of resin bleed that is desired. The fluorinated ethylene propylene (FEP) film 72*c* may comprise a type of release film 72*b*. The release film 72*b* and FEP film 72*c* may both preferably be removed following cure of the composite structure 28 (see FIG. 1), so that there is no contamination of the composite structure 28 (see FIG. 1), such as the aircraft composite part 28*a* (see FIG. 1).

The caul plate 72*d* (see FIG. 4) or caul sheet may comprise smooth plates, free of surface defects, and may be made of metal materials, thin composite materials, or elastomeric materials, and may be the same size and shape as the composite lay-up, and may be used in contact with the composite lay-up during the curing process. The caul plate 72*d* (see FIG. 4) transmits normal pressure and temperature, and provides a smooth surface on the finished composite structure 28 (see FIG. 4). After the curing process, the caul plate 72*d* (see FIG. 4) or caul sheet is preferably removed from the composite lay-up 70 (see FIG. 4)), so that there is no contamination of the composite structure 28 (see FIG. 1), such as the aircraft composite part 28*a* (see FIG. 1).

The first series of probes 66*a* (see FIG. 4) of the thermochromatic material 68 (see FIG. 4), or alternatively, the first series of probes 66*a* (see FIG. 4) and the second series of probes 66*b* (see FIG. 4) of the thermochromatic material 68 (see FIG. 4), may be applied either via spraying, or via mixing into a pre-preg resin 78 (see FIG. 4) of the composite lay-up 70 to form a thermochromatic resin 80 (see FIG. 4), or via another suitable application process.

As shown in FIG. 4, the system 10 may comprise a sprayer apparatus 82 to spray or apply the first series of probes 66*a* of the thermochromatic material 68, or to spray or apply both the first series of probes 66*a* and the second series of probes 66*b* of the thermochromatic material 68. The first series of probes 66*a* (see FIG. 4) of the thermochromatic material 68 (see FIG. 4) may be supplied to the sprayer apparatus 82 (see FIG. 4) from a first supply source 86 (see FIG. 4), and the second series of probes 66*b* (see FIG. 4) of the thermochromatic material 68 (see FIG. 4) may be supplied to the sprayer apparatus 82 (see FIG. 4) from a second supply source 88 (see FIG. 4). The removable material 72 (see FIG. 4), such as, for example, in the form of peel ply 72*a* (see FIG. 4), is preferably sprayed with the thermochromatic material 68 (see FIG. 4) from the sprayer apparatus 82 (see FIG. 4), to form a thermochromatic coating 84 (see FIG. 4) on the removable material 72 (see FIG. 4) and to obtain a thermochromatic coated removable material 73 (see FIG. 4). The thermochromatic material 68 (see FIG. 4) may also be applied directly to the composite lay-up 70 (see FIG. 4) that is laid up on a tool 90 (see FIG. 4) or mold, and preferably is applied directly to a surface 74 (see FIG. 4) of the composite lay-up 70 (see FIG. 4) after the composite lay-up 70 (see FIG. 4) is laid up, but before it is processed in a vacuum bag assembly 100 (see FIG. 4) and in an autoclave 106 (see FIG. 4) and cured. The composite lay-up 70 (see FIG. 4) laid up on the tool 90 (see FIG. 4) and sprayed with the thermochromatic material 68 (see FIG. 4) from the sprayer apparatus 82 (see FIG. 4) forms the thermochromatic coating 84 (see FIG. 4) on the composite lay-up 70 (see FIG. 4) and obtains a thermochromatic coated composite lay-up 71 (see FIG. 4). The thermochromatic material 68 (see FIG. 4) may also be applied directly to a surface 96 (see FIG. 4) of the tool 90 (see FIG. 4) or mold to verify a tool thermal profile 138 (see FIG. 4), discussed in further detail below, of the tool 90 (see FIG. 4). The tool 90 (see FIG. 4) sprayed with the thermochromatic material 68 (see FIG. 4) from the sprayer apparatus 82 (see FIG. 4) forms the thermochromatic coating 84 (see FIG. 4) on the tool 90 (see FIG. 4) and obtains a thermochromatic coated tool 91 (see FIG. 4). The thermochromatic material 68 (see FIG. 4) may be sprayed in a pattern, over the entire surface that is sprayed, or over a portion of the surface that is sprayed. The thermochromatic material 68 (see FIG. 4) may be sprayed at ambient temperature. Preferably, one layer or coating of the thermochromatic material 68 is sprayed on one side, or a portion of one side, of the material to be coated, and preferably the visual or viewable side is sprayed or coated. With the thermochromatic resin 80 (see FIG. 4), one or both sides, or portions of one or both sides, of the material to be coated may be coated with the thermochromatic resin 80 (see FIG. 4).

Figure 5A:
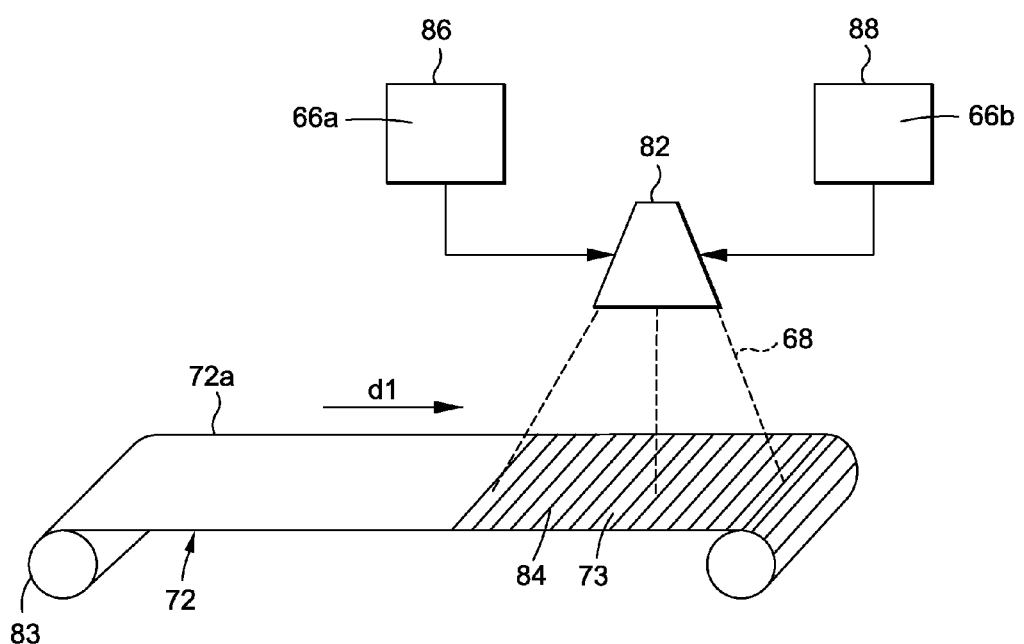
FIG. 5A is a diagrammatic representation of a schematic diagram of a removable material sprayed with a thermochromatic material from a sprayer apparatus.

In one embodiment, as shown in FIG. 5A, the thermochromatic material 68 is applied to the removable material 72. FIG. 5A is a diagrammatic representation of a schematic diagram of the removable material 72, such as, for example, in the form of peel ply 72*a*, sprayed with the thermochromatic material 68 from the sprayer apparatus 82, to form the thermochromatic coating 84 on the removable material 72 and to obtain the thermochromatic coated removable material 73. As shown in FIG. 5A, the first series of probes 66*a* of the thermochromatic material 68 may be supplied to the sprayer apparatus 82 from the first supply source 86, and the second series of probes 66*b* of the thermochromatic material 68 may be supplied to the sprayer apparatus 82 from the second supply source 88. As shown in FIG. 5A, the removable material 72 may be formed in a roll, attached to a roller apparatus 83, and rolled in a direction ($d_1$) toward the sprayer apparatus 82. The removable material 72 (see FIG. 5A) that is coated with the thermochromatic material 68 (see FIG. 5A) is then preferably laid up adjacent to the composite lay-up 70 (see FIG. 6A), which is preferably laid up on the tool 90 or mold, to form the thermochromatic witness assembly 64. Alternatively, the removable material 72, such as in the form of peel ply 72*a*, may already be coated, or previously coated, with the thermochromatic material 68, and supplied in rolled configuration or in another suitable configuration. For in-process applications, the embodiment shown in FIG. 5A allows for validation of the composite structure 28 curing, which may eliminate the need for process control tests.

Figure 5B:
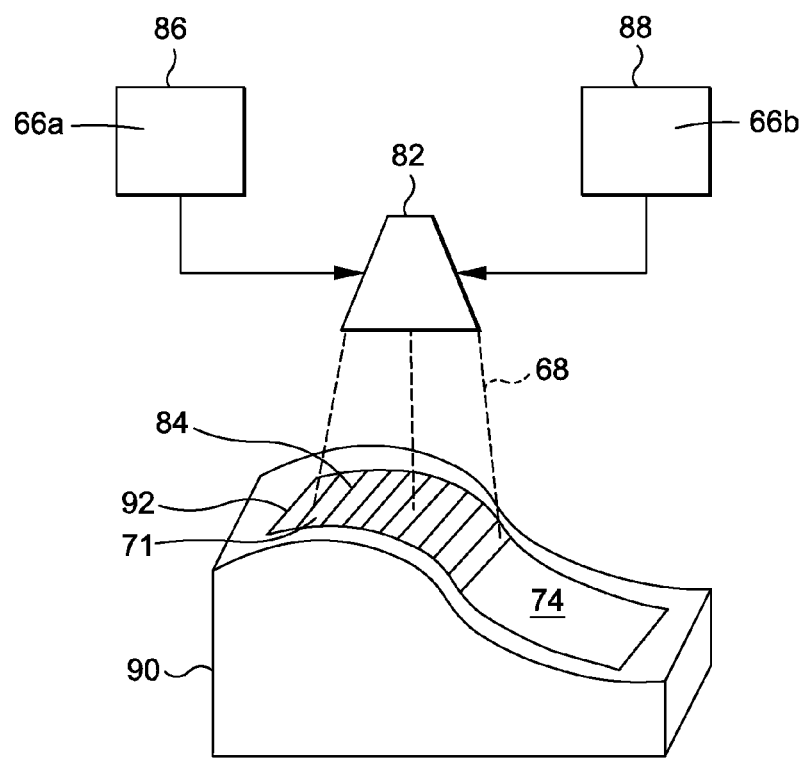
FIG. 5B is a diagrammatic representation of a schematic diagram of a composite lay-up on a tool sprayed with a thermochromatic material from a sprayer apparatus.

In another embodiment, as shown in FIG. 5B, the thermochromatic material 68 is applied directly to the composite lay-up 70 that is laid up on the tool 90 or mold, and preferably is applied directly to the surface 74 of the composite lay-up 70 after the composite lay-up 70 is laid up but before it is processed in the vacuum bag assembly 100 (see FIG. 4) and in the autoclave 106 (see FIG. 4) and cured. FIG. 5B is a diagrammatic representation of a schematic diagram of the composite lay-up 70 laid up on the tool 90 and sprayed with the thermochromatic material 68 from the sprayer apparatus 82 to form the thermochromatic coating 84 on the composite lay-up 70 and to obtain the thermochromatic coated composite lay-up 71. As further shown in FIG. 5B, the first series of probes 66a of the thermochromatic material 68 may be supplied to the sprayer apparatus 82 from the first supply source 86, and the second series of probes 66b of the thermochromatic material 68 may be supplied to the sprayer apparatus 82 from the second supply source 88.

As further shown in FIG. 5B, the composite lay-up 70 that is coated with the thermochromatic material 68 may be in the form of a developmental part 92. The thermochromatic material 68 (see FIG. 5B) may be applied directly to the developmental part 92 via either spraying, or mixing with the pre-preg resin 78 (see FIG. 4) to form the thermochromatic resin 80 (see FIG. 4). By applying the thermochromatic material 68 (see FIG. 5B) directly to the composite lay-up 70 (see FIG. 5B), such as in the form of developmental part 92 (see FIG. 5B), it is possible to quickly determine the thermal profile 62 (see FIG. 4), such as temperature profile(s) 94 (see FIG. 4), of the composite lay-up 70 (see FIGS. 4, 5B), such as in the form of developmental part 92 (see FIGS. 4, 5B), and to guide the design of the tool 90 (see FIGS. 4, 5B) and future process parameters.

For in-process applications, the embodiment shown in FIG. 5B allows for validation of the composite structure 28 curing, which may eliminate the need for process control tests and may also aid and expedite material review board (MRB) processes, and may solve heating issues. The thermochromatic material 68 (see FIG. 4) may also be applied outside of the aircraft composite part 28a (see FIGS. 1, 4) areas for in-process monitoring and validation of the cure cycle. In this case, the thermochromatic material 68 (see FIG. 4) is still applied to the composite structure 28 but would be outside the area trimmed to become the composite part, such as the aircraft composite part 28a (see FIG. 1), and would be on an area that is trimmed.

Figure 5C:
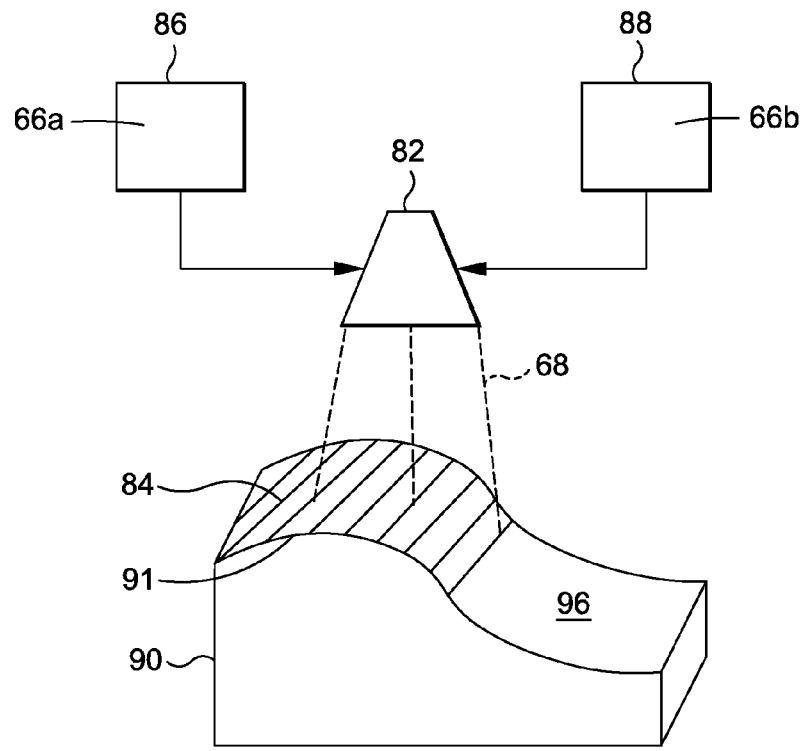
FIG. 5C is a diagrammatic representation of a schematic diagram of a tool sprayed with a thermochromatic material from a sprayer apparatus.

In another embodiment, as shown in FIG. 5C, the thermochromatic material 68 is applied directly to the surface 96 of the tool 90 or mold to verify a tool thermal profile 138 (see FIG. 4), discussed in further detail below, of the tool 90. FIG. 5C is a diagrammatic representation of a schematic diagram of the tool 90 sprayed with the thermochromatic material 68 from the sprayer apparatus 82 to form the thermochromatic coating 84 on the tool 90 and to obtain the thermochromatic coated tool 91. As further shown in FIG. 5C, the first series of probes 66a of the thermochromatic material 68 may be supplied to the sprayer apparatus 82 from the first supply source 86, and the second series of probes 66b of the thermochromatic material 68 may be supplied to the sprayer apparatus 82 from the second supply source 88.

Figure 6A:
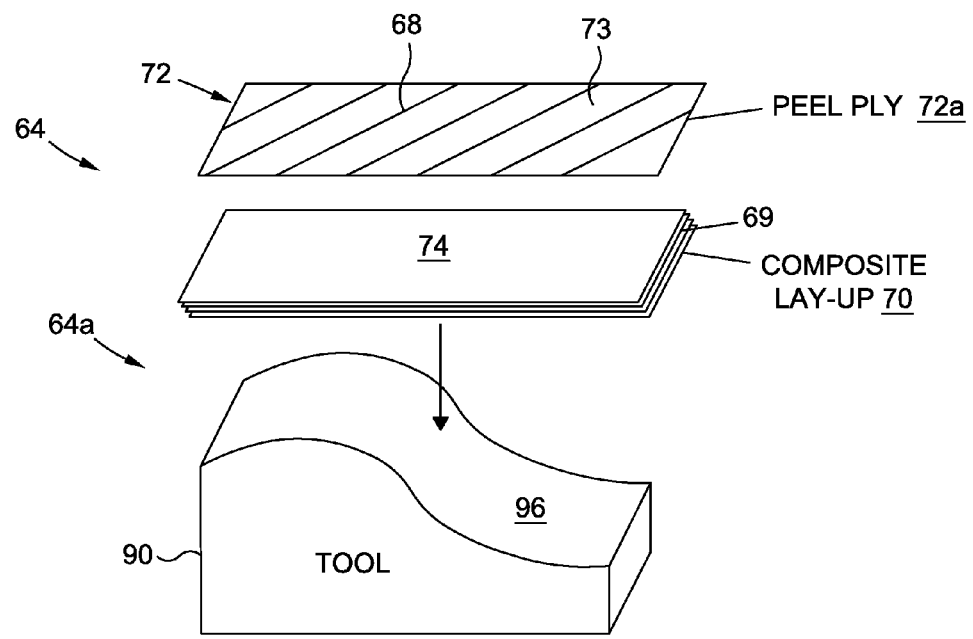
FIGS. 6A-6E are diagrammatic representations of various exemplary thermochromatic witness assemblies that may be used in the system of the disclosure.
Figure 6B:
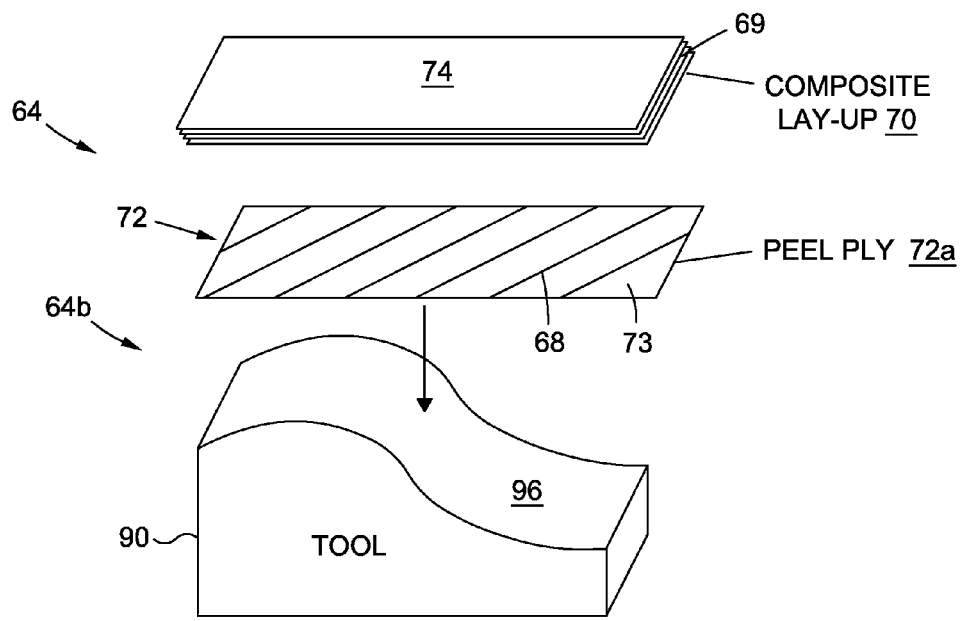

FIGS. 6A-6E are diagrammatic representations of various exemplary thermochromatic witness assemblies 64, without limitation, that may be used in the system 10 of the disclosure. FIG. 6A shows a thermochromatic witness assembly 64, such as in the form of thermochromatic witness assembly 64a, comprising the composite lay-up 70 configured and intended to be laid up on the tool 90, with the thermochromatic coated removable material 73, such as a peel ply 72a coated with the thermochromatic material 68, configured and intended to be laid up over the surface 74 of the composite lay-up 70. FIG. 6B shows a thermochromatic witness assembly 64, such as in the form of thermochromatic witness assembly 64b, comprising the thermochromatic coated removable material 73, such as a peel ply 72a coated with the thermochromatic material 68, configured and intended to be laid up over the surface 96 of the tool 90 and the composite lay-up 70 configured and intended to be laid up over the thermochromatic coated removable material 73, such as a peel ply 72a coated with the thermochromatic material 68.

The thermochromatic material 68 (see FIG. 4) may be applied to the peel ply 72a (see FIG. 4), or in the pre-preg resin 78 (see FIG. 4) of the peel ply 72a (see FIG. 4), to thermally map the thermal profile 62 (see FIG. 4) on developmental parts or production parts. The peel ply 72a (see FIG. 4) is examined, photographed with a camera 120 (see FIG. 4) under a light source 112 (see FIG. 4), such as a UV light source 112a (see FIG. 4) for documentation, and then removed from the composite structure 28, such as the aircraft composite part 28a. Results may be used to modify and improve the composite structure 28, such as the aircraft composite part 28a (see FIG. 4), the tool 90 (see FIG. 4), or other processes.

Figure 6C:
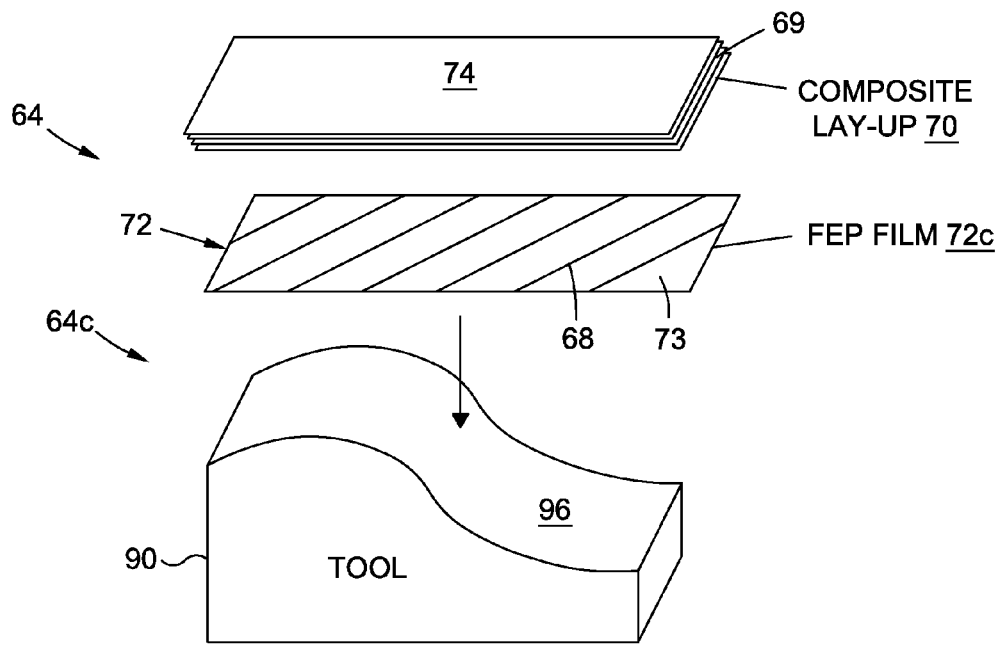
Figure 6D:
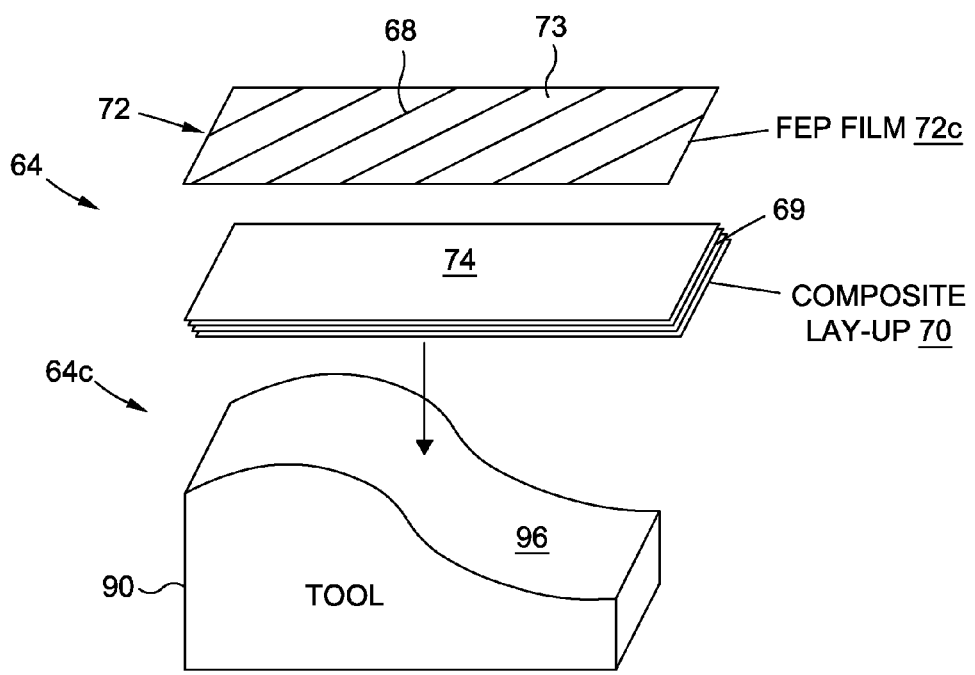

FIG. 6C shows a thermochromatic witness assembly 64, such as in the form of thermochromatic witness assembly 64c, comprising the thermochromatic coated removable material 73, such as the fluorinated ethylene propylene (FEP) film 72c coated with the thermochromatic material 68, configured and intended to be laid up over the surface 96 of the tool 90 and the composite lay-up 70 configured and intended to be laid up over the thermochromatic coated removable material 73, such as the FEP film 72c coated with the thermochromatic material 68. FIG. 6D shows a thermochromatic witness assembly 64, such as in the form of thermochromatic witness assembly 64d, comprising the composite lay-up 70 configured and intended to be laid up on the tool 90 with the thermochromatic coated removable material 73, such as the FEP film 72c coated with the thermochromatic material 68, configured and intended to be laid up over the surface 74 of the composite lay-up 70.

The thermochromatic material 68 (see FIG. 4) may be applied to the FEP film 72c (see FIG. 4) or to the release film 72b (see FIG. 4), that are preferably removed after examination and documentation. The activated thermochromatic material 130 (see FIG. 4) applied to the FEP film 72c (see FIG. 4) or to the release film 72b (see FIG. 4) may be inspected on the tool 90 (see FIG. 4), or alternatively, on the composite structure 28, such as the aircraft composite part 28a, under the light source 112 (see FIG. 4), such as the UV light source 112a (see FIG. 4), photographed for documentation, and then removed.

Figure 6E:
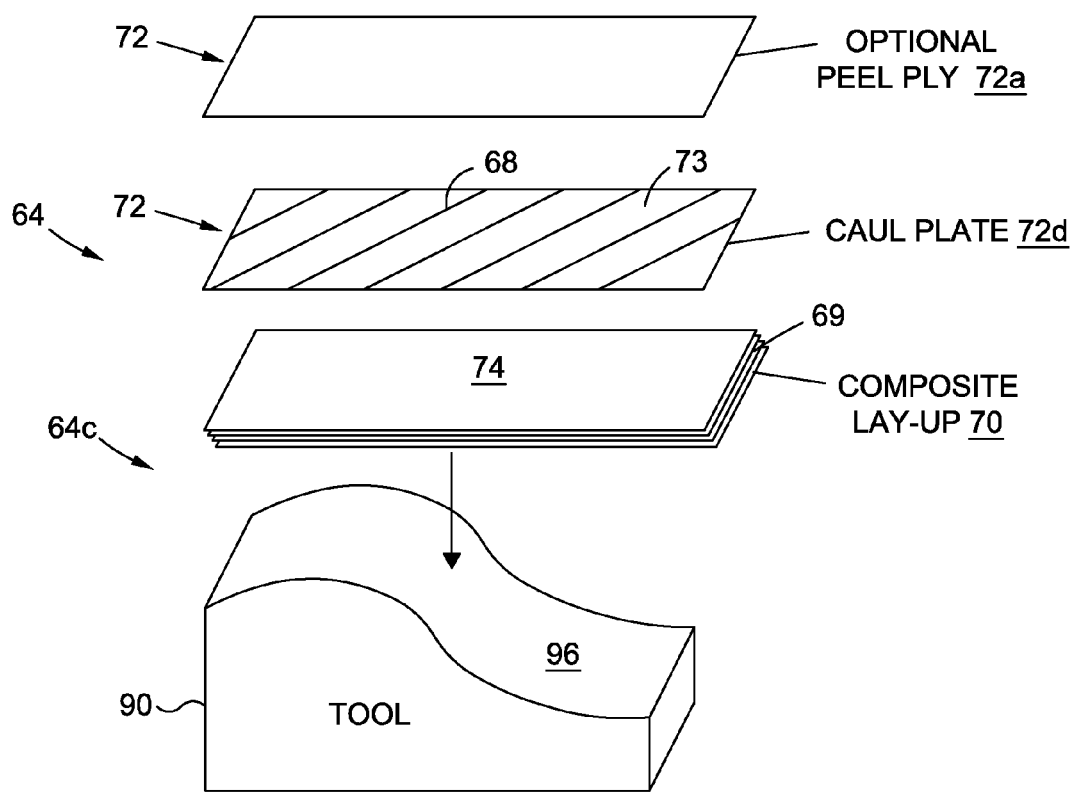

FIG. 6E shows a thermochromatic witness assembly 64, such as in the form of thermochromatic witness assembly 64e, comprising the composite lay-up 70 configured and intended to be laid up on the tool 90 with the thermochromatic coated removable material 73, such as the caul plate 72d coated with the thermochromatic material 68, configured and intended to be laid up over the surface 74 of the composite lay-up 70. The caul plate 72d (see FIG. 6E) may be used in place of a peel ply 72a (see FIG. 6A) or in addition to a peel ply 72a (see FIG. 6E). If the caul plate 72d (see FIG. 6E) is used in addition to the peel ply 72a (see FIG. 6E), the peel ply 72a (see FIG. 6E) may be laid up over the caul plate 72d (see FIG. 6E) or the caul plate 72d may be laid up over the peel ply 72a, and whichever is adjacent to the composite lay-up 70 (see FIG. 6E) is preferably coated with the thermochromatic material 68 (see FIG. 6E).

The thermochromatic material 68 (see FIG. 4) may be applied to the caul plate 72d (see FIG. 4), where a caul plate is used, and the caul plate 72d (see FIG. 4) is preferably removed after examination and documentation. The activated thermochromatic material 130 (see FIG. 4) applied to the caul plate 72d (see FIG. 4) may be inspected on the tool 90 (see FIG. 4), or alternatively, on the composite structure 28, such as the aircraft composite part 28a, under the light source 112 (see FIG. 4), such as the UV light source 112a (see FIG. 4), photographed for documentation, and then removed.

Figure 7:
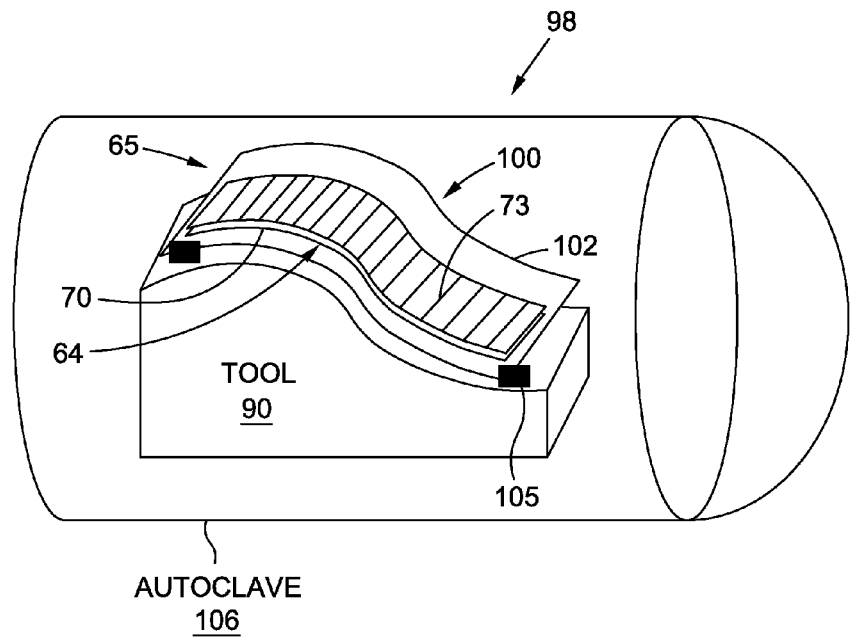
FIG. 7 is a diagrammatic representation of a bagged thermochromatic witness assembly in an autoclave.

As shown in FIGS. 4 and 7, the system 10 further comprises a process assembly 98 for processing the thermochromatic witness assembly 64, such as in the form of a vacuum bag assembly 100. FIG. 7 is a diagrammatic representation of a bagged thermochromatic witness assembly 65 of the vacuum bag assembly 100 and in an autoclave 106. The process assembly 98 (see FIGS. 4, 7) preferably comprises a manufacturing process assembly 98a (see FIG. 4) or a repair process assembly 98b (see FIG. 4). The process assembly 98 (see FIG. 4) may comprise the vacuum bag assembly 100 (see FIGS. 4, 7) having a vacuum bag 102 (see FIGS. 4, 7) and bagging materials 104 (see FIG. 4). The vacuum bag 102 (see FIG. 7) may be placed over the thermochromatic witness assembly 64 (see FIG. 7) and any additional bagging materials 104 (see FIG. 4) and is preferably sealed to the tool 90 (see FIG. 7) using any suitable sealing devices, such as sealant tape 105 (see FIG. 7) to form the bagged thermochromatic witness assembly 65 (see FIG. 7). The bagged thermochromatic witness assembly 65 (see FIG. 7) may then preferably be placed in the autoclave 106 (see FIG. 7), in an oven, or in another suitable heating apparatus having a heat source 108 (see FIG. 4).

The process assembly 98 (see FIG. 4) may further comprise the heat source 108 (see FIG. 4) which is configured to cure the thermochromatic witness assembly 64 (see FIG. 4) with heat 110 (see FIG. 4) to form the composite structure 28 (see FIG. 4). The vacuum bag assembly 100 (see FIGS. 4, 7) with the thermochromatic witness assembly 64 (see FIGS. 4, 7) is preferably subjected to an elevated temperature and pressure, and the vacuum bag 102 (see FIGS. 4, 7) is preferably evacuated, which causes the vacuum bag 102 (see FIGS. 4, 7) to apply compaction pressure to the composite lay-up 70 (see FIGS. 4, 7). During curing in the autoclave 106 (see FIGS. 4, 7), pressure in the autoclave 106 (see FIGS. 4, 7) assists in compacting and consolidating the composite lay-up 70 (see FIGS. 4, 7).

After the composite structure 28 (see FIG. 4) is cured, the composite structure 28 (see FIG. 4) is removed from the autoclave 106 (see FIGS. 4, 7), oven or other suitable heating apparatus, and is preferably removed from the tool 90 (see FIGS. 4, 7). The cured composite structure 28 (see FIG. 4) is then placed in close proximity to a light source 112 (see FIGS. 4, 8), so that the thermochromatic material 68 (see FIGS. 4, 7) of the thermochromatic witness assembly 64 (see FIGS. 4, 7) may be activated.

Figure 8:
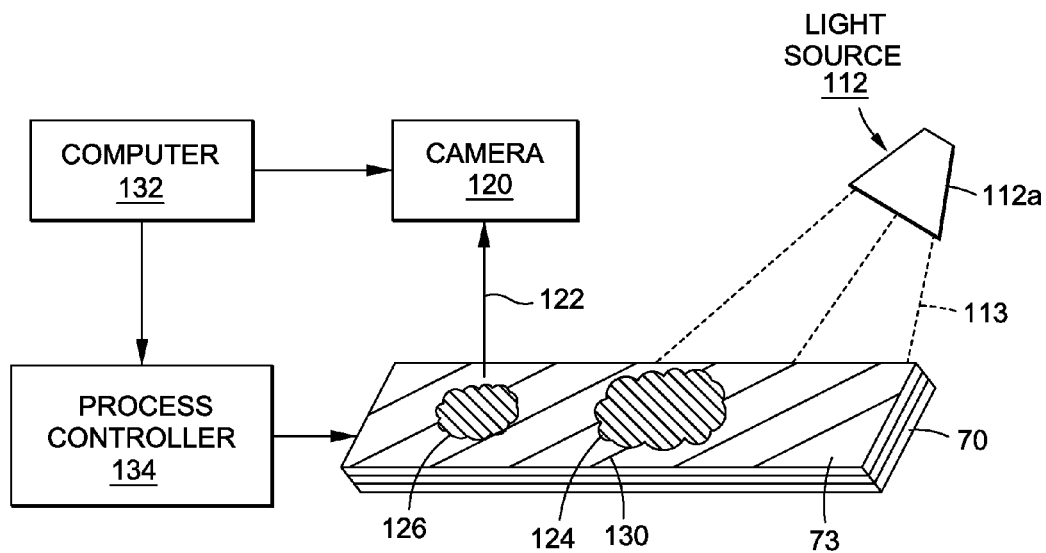
FIG. 8 is a diagrammatic representation of an activated thermochromatic material illuminated by a light source.

As shown in FIGS. 4 and 8, the system 10 further comprises the light source 112 configured to activate the thermochromatic material 68. FIG. 8 is a diagrammatic representation of an activated thermochromatic material 130 illuminated by illumination 113 from the light source 112. The light source 112 preferably comprises at least one of an ultraviolet (UV) light source 112a (see FIGS. 4, 8), an infrared (IR) light source 112b (see FIG. 4), an optical light source 112c (see FIG. 4), and another suitable light source 112. "At least one of" means either only an ultraviolet (UV) light source 112a (see FIGS. 4, 8), only an infrared (IR) light source 112b (see FIG. 4), only an optical light source 112c (see FIG. 4), or only another suitable light source 112, or any combination of an ultraviolet (UV) light source 112a (see FIGS. 4, 8), an infrared (IR) light source 112b (see FIG. 4), an optical light source 112c (see FIG. 4), and another suitable light source 112. The light source 112 (see FIGS. 4, 8) illuminates the thermochromatic material 68 (see FIG. 4) with illumination 113 (see FIG. 8) of light of a preselected wavelength, such as in the ultraviolet (UV) or infrared (IR) range.

The light source 112 (see FIGS. 4, 8) is configured to activate the thermochromatic material 68 (see FIG. 4) of the first series of probes 66a (see FIG. 4) to prompt an onset of color changes 114 (see FIG. 4) in the thermochromatic material 68 (see FIG. 4). The color changes 114 (see FIG. 4) in the thermochromatic material 68 (see FIG. 4) are preferably used to determine one or more maximum temperature (s) 116 (see FIG. 4) of the composite structure 28 (see FIG. 4), in order to map the thermal profile 62 (see FIG. 4) of the composite structure 28 (see FIG. 4) during manufacture or repair of the composite structure 28 (see FIG. 4). The color changes 114 (see FIG. 4) may indicate that the composite structure 28 (see FIG. 4) has been subjected to temperatures outside the desired range of values. Thus, the thermochromatic material 68 (see FIG. 4) acts as a "witness" that indicates out-of-range process parameters that may be used to assess the suitability of the formed composite structure 28, or to adjust the process parameters.

In the embodiment where the thermochromatic witness assembly 64 (see FIG. 4) comprises the second series of probes 66b (see FIG. 4), the light source 112 (see FIG. 4) is configured to activate the thermochromatic material 68 (see FIG. 4) of the second series of probes 66b (see FIG. 4) to provide a time-temperature profile 118 (see FIG. 4). The second series of probes 66b (see FIG. 4) may be used to determine the relative change between a temperature at which the first series of probes 66a (see FIG. 4) are activated and a temperature at which the second series of probes 66b (see FIG. 4) are activated. The first series of probes 66a (see FIG. 4) and the second series of probes 66b (see FIG. 4) of the thermochromatic material 68 (see FIG. 4) may be used to map and monitor process parameters, such as temperature, during the cure cycle to determine if the temperature is outside of a predetermined range of values.

As shown in FIGS. 4 and 8, the system 10 may further comprise a camera 120 to record one or more images 122 of the activated thermochromatic material 130 comprising the thermochromatic material 68 (see FIG. 4) of the first series of probes 66a (see FIG. 4) and/or the second series of probes 66b (see FIG. 4) after activation with the light source 112. The camera 120 (see FIG. 4) may comprise a digital camera or another suitable recording device. The activated thermochromatic material 130 (see FIG. 8) is preferably inspected under or in close proximity to the light source 112 (see FIGS. 4, 8) to inspect for hot areas 124 (see FIGS. 4, 8), cold areas 126 (see FIGS. 4, 8), and thermal trends 128 (see FIG. 4). Results of any hot areas 124 (see FIGS. 4, 8), cold areas 126 (see FIGS. 4, 8), and thermal trends 128 (see FIG. 4) may be photographed with the camera 120 (see FIGS. 4, 8) and documented.

As further shown in FIGS. 4 and 8, a computer 132 may be used to store the one or more images 122 in a memory. Based on the one or more images 122 (see FIGS. 4, 8) recorded by the camera 120 (see FIGS. 4, 8), the computer 132 (see FIGS. 4, 8) may provide information to a process controller 134 (see FIGS. 4, 8) that may adjust process parameters, such as temperature, to improve the process assembly 98 (see FIG. 4), the tool 90 (see FIG. 4), or the composite structure 28 (see FIG. 4).

As shown in FIG. 4, the system 10 may further comprise a tool verification assembly 136 configured to verify a tool thermal profile 138 of the tool 90. The tool verification assembly 136 comprises the tool 90 configured for receiving the composite lay-up 70 or the composite lay-up 70 with the removable material 72 adjacent the composite lay-up 70. The tool verification assembly 136 further comprises the first series of probes 66a comprising the thermochromatic material 68, or the first series of probes 66a and the second series of probes 66b comprising the thermochromatic material 68, applied directly to a surface 96 of the tool 90 or mold. The tool verification assembly 136 further comprises the light source 112 configured to activate the thermochromatic material 68 of the first series of probes 66a, or the first series of probes 66a and the second series of probes 66b, to verify the tool thermal profile 138 of the tool 90.

The thermochromatic material 68 (see FIG. 4) may also be applied outside of the aircraft composite part 28a (see FIGS. 1, 4) areas for in-process monitoring and validation of the cure cycle.

Figure 9:
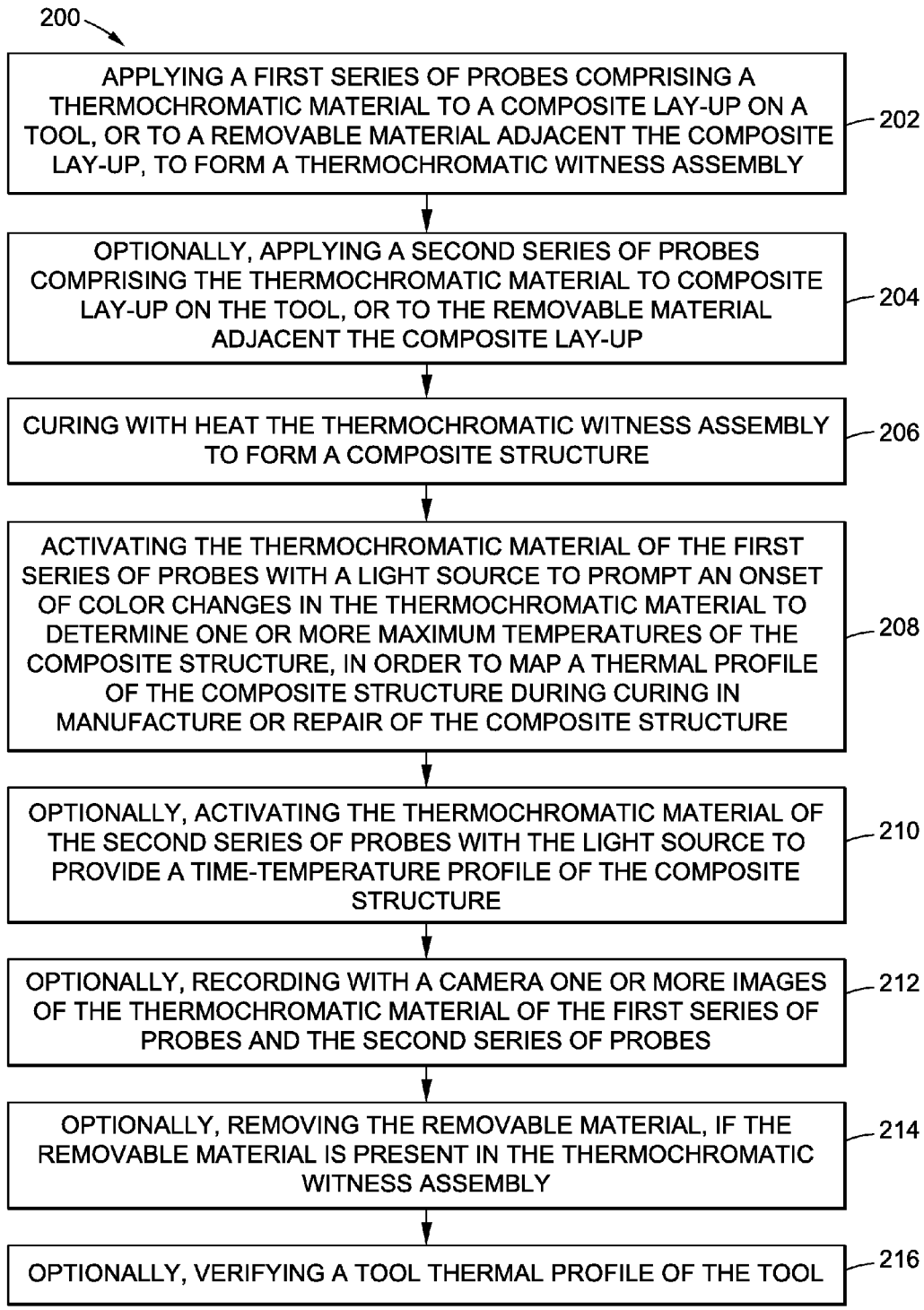
FIG. 9 is a flow diagram showing an embodiment of a method of the disclosure.

In another embodiment, as shown in FIG. 9, there is provided a method 200 to map a thermal profile 62 (see FIG. 4) of a composite structure 28 (see FIG. 4) during curing in at least one of manufacture of the composite structure 28, or repair of the composite structure 28. "At least one of" may mean only manufacture of the composite structure 28, or only repair of the composite structure 28, or a combination of manufacture of the composite structure 28 and repair of the composite structure 28 (see FIG. 4). FIG. 9 is a flow diagram showing an embodiment of the method 200 of the disclosure.

As shown in FIG. 9, the method 200 comprises step 202 of applying a first series of probes 66a (see FIG. 4) comprising a thermochromatic material 68 (see FIG. 4) either to a composite lay-up 70 (see FIG. 4) on a tool 90 (see FIG. 4), and preferably to a surface 74 (see FIG. 4) of the composite lay-up 70 (see FIG. 4), or to a removable material 72 (see FIG. 4) adjacent the composite lay-up 70 (see FIG. 4), and preferably to a surface 76 (see FIG. 4) of the removable material 72 (see FIG. 4), to form a thermochromatic assembly 64 (see FIGS. 4, 6A-6E). The step 202 of applying the first series of probes 66a (see FIG. 4) further comprises the step of applying the first series of probes 66a (see FIG. 4) to the removable material 72 (see FIG. 4), which comprises at least one of a peel ply 72a (see FIGS. 4, 6A), a release film 72b (see FIG. 4), a fluorinated ethylene propylene (FEP) film 72c (see FIG. 4), or a caul plate 72d (see FIG. 4), adjacent the composite lay-up 70 (see FIG. 4).

As shown in FIG. 9, the method 200 may further comprise optional step 204 of applying a second series of probes 66b (see FIG. 4) comprising the thermochromatic material 68 (see FIG. 4) either to the composite lay-up 70 (see FIG. 4), and preferably to the surface 74 (see FIG. 4) of the composite lay-up 70 (see FIG. 4), or to the removable material 72 (see FIG. 4) adjacent the composite lay-up 70 (see FIG. 4), and preferably to the surface 76 (see FIG. 4) of the removable material 72 (see FIG. 4). The step 202 of applying the first series of probes 66a and the optional step 204 of applying the second series of probes 66b may comprise either by spraying, or mixing into a pre-preg resin 78 of the composite lay-up 70 to form a thermochromatic resin 80, or another suitable application method.

As shown in FIG. 9, the method 200 further comprises step 206 of curing with heat 110 (see FIG. 4) the thermochromatic witness assembly 64 (see FIGS. 4, 6A-6E) to form the composite structure 28 (see FIG. 4). The cure time, cure temperature and cure pressure depend on the materials of the composite lay-up 70 and the resin system used.

As shown in FIG. 9, the method 200 further comprises step 208 of activating the thermochromatic material 68 (see FIG. 4) of the first series of probes 66a (see FIG. 4) with a light source 112 (see FIGS. 4, 8) to prompt an onset of color changes 114 (see FIG. 4) in the thermochromatic material 68 (see FIG. 4) to determine one or more maximum temperatures 116 (see FIG. 4) of the composite structure 28 (see FIG. 4), in order to map the thermal profile 62 (see FIG. 4) of the composite structure 28 (see FIG. 4) during curing in at least one of the manufacture of the composite structure 28 (see FIG. 4), or repair of the composite structure 28 (see FIG. 4).

The step 208 of activating the thermochromatic material 68 (see FIG. 4) further comprises activating the thermochromatic material 68 (see FIG. 4) of the first series of probes 66a (see FIG. 4) with the light source 112 (see FIG. 4) to prompt the onset of color changes 114 (see FIG. 4) and retaining the color changes 114 (see FIG. 4) in the removable material 72 (see FIG. 4) for one or more hours after the composite structure 28 (see FIG. 4) returns to a nominal temperature 95 (see FIG. 4).

The step 208 of activating the thermochromatic material 68 (see FIG. 4) of the first series of probes 66a (see FIG. 4) with the light source 112 (see FIG. 4) further comprises activating the thermochromatic material 68 (see FIG. 4) of the first series of probes 66a (see FIG. 4) with the light source 112 (see FIG. 4) comprising an ultraviolet (UV) light source 112a (see FIG. 4), an infrared (IR) light source 112b (see FIG. 4), an optical light source 112c (see FIG. 4), or another suitable light source.

As shown in FIG. 9, the method 200 may further comprise optional step 210 of activating the thermochromatic material 68 of the second series of probes 66b with the light source 112 (see FIGS. 4, 8). The second series of probes 66b (see FIG. 4) is preferably configured to provide a time-temperature profile 118 (see FIG. 4) of the composite structure 28 (see FIG. 4).

As further shown in FIG. 9, the method 200 may further comprise after the step 208 of activating the thermochromatic material 68 (see FIG. 4) of the first series of probes 66a (see FIG. 4) or after the optional step 210 of activating the thermochromatic material 68 (see FIG. 4) of the second series of probes 66b (see FIG. 4), the optional step 212 of recording with a camera 120 (see FIGS. 4, 8) one or more images 122 (see FIGS. 4, 8) of the thermochromatic material 68 (see FIG. 4) of the first series of probes 66a (see FIG. 4) and the second series of probes 66b (see FIG. 4).

As further shown in FIG. 9, the method 200 may further comprise after the optional step 212 of recording with the camera 120 (see FIGS. 4, 8) one or more images 122 (see FIGS. 4, 8), the optional step 214 of removing the removable material 72 (see FIG. 4), if the removable material 72 (see FIG. 4) is present in the thermochromatic witness assembly 64 (see FIGS. 4, 6A-6E).

As further shown in FIG. 9, the method 200 may further comprise the optional step 216 of verifying a tool thermal profile 138 (see FIG. 4) of the tool 90 (see FIG. 4). The optional step 216 of verifying the tool thermal profile 138 (see FIG. 4) preferably comprises the steps of applying the first series of probes 66a (see FIG. 4) comprising the thermochromatic material 68 (see FIG. 4) to a surface 96 (see FIG. 4) of the tool 90 (see FIG. 4) and activating the thermochromatic material 68 (see FIG. 4) of the first series of probes 66a (see FIG. 4) with the light source 112 (see FIG. 4) to verify the tool thermal profile 138 (see FIG. 4) of the tool 90 (see FIG. 4). The optional step 216 of verifying the tool thermal profile 138 (see FIG. 4) may further comprise the steps of applying the second series of probes 66b (see FIG. 4) comprising the thermochromatic material

68 (see FIG. 4) to the surface 96 (see FIG. 4) of the tool 90 (see FIG. 4) and activating the thermochromatic material 68 (see FIG. 4) of the second series of probes 66b (see FIG. 4) with the light source 112 (see FIG. 4) to verify the tool thermal profile 138 (see FIG. 4) of the tool 90 (see FIG. 4).

Figure 10:
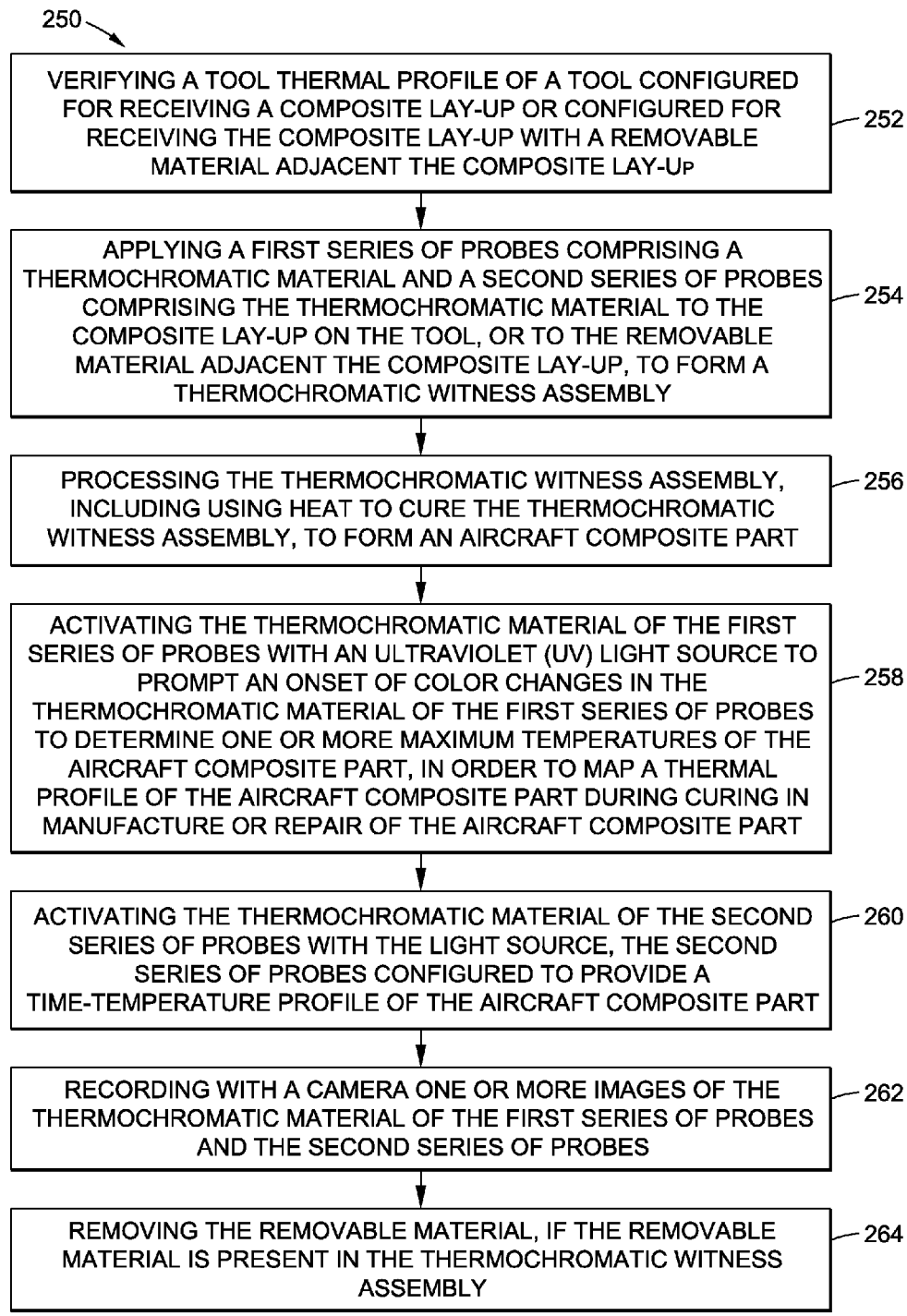
FIG. 10 is a flow diagram showing another embodiment of a method of the disclosure.

In another embodiment, as shown in FIG. 10, there is provided a method 250 to map a thermal profile 62 (see FIG. 4) of an aircraft composite part 28a (see FIG. 1) during curing in at least one of manufacture of the aircraft composite part 28a (see FIG. 1), or repair of the aircraft composite part 28a (see FIG. 1). "At least one of" may mean only manufacture of the aircraft composite part 28a, or only repair of the aircraft composite part 28a, or a combination of manufacture of the aircraft composite part 28a and repair of the aircraft composite part 28a (see FIG. 1). FIG. 10 is a flow diagram showing another embodiment of a method 250 of the disclosure.

As shown in FIG. 10, the method 250 comprises step 252 of verifying a tool thermal profile 138 (see FIG. 4) of a tool 90 see FIG. 4) configured for receiving a composite lay-up 70 see FIG. 4) or configured for receiving the composite lay-up 70 see FIG. 4) with a removable material 72 see FIG. 4) adjacent the composite lay-up 70 (see FIG. 4).

As shown in FIG. 10, the method 250 further comprises step 254 of applying a first series of probes 66a (see FIG. 4) comprising a thermochromatic material 68 (see FIG. 4) and a second series of probes 66b (see FIG. 4) comprising the thermochromatic material 68 (see FIG. 4) either to a composite lay-up 70 (see FIG. 4) on the tool 90 (see FIG. 4), and preferably to a surface 74 (see FIG. 4) of the composite lay-up 70 (see FIG. 4), or to a removable material 72 (see FIG. 4) adjacent the composite lay-up 70 (see FIG. 4), and preferably to a surface 76 (see FIG. 4) of the removable material 72 (see FIG. 4), to form a thermochromatic witness assembly 64 (see FIG. 4).

As shown in FIG. 10, the method 250 further comprises step 256 of processing the thermochromatic witness assembly 64, including using heat 110 (see FIG. 4) to cure the thermochromatic witness assembly 64 (see FIG. 4), to form the aircraft composite part 28a (see FIG. 1). The cure time, cure temperature and cure pressure depend on the materials of the composite lay-up 70 and the resin system used.

As shown in FIG. 10, the method 250 further comprises step 258 of activating the thermochromatic material 68 (see FIG. 4) of the first series of probes 66a (see FIG. 4) with an ultraviolet (UV) light source 112a (see FIG. 4) to prompt an onset of color changes 114 (see FIG. 4) in the thermochromatic material 68 (see FIG. 4) of the first series of probes 66a (see FIG. 4) to determine one or more maximum temperatures 116 (see FIG. 4) of the aircraft composite part 28a (see FIG. 1), in order to map the thermal profile 62 (see FIG. 4) of the aircraft composite part 28a (see FIG. 1) during curing in at least one of manufacture or repair of the aircraft composite part 28a (see FIG. 1).

As shown in FIG. 10, the method 250 further comprises step 260 of activating the thermochromatic material 68 (see FIG. 4) of the second series of probes 66b (see FIG. 4) with the light source 112 (see FIG. 4), the second series of probes 66b (see FIG. 4) configured to provide a time-temperature profile 118 (see FIG. 4) of the aircraft composite part 28a (see FIG. 1).

As shown in FIG. 10, the method 250 further comprises step 262 of recording with a camera 120 (see FIG. 8) one or more images 122 (see FIG. 8) of the thermochromatic material 68 (see FIG. 4) of the first series of probes 66a (see FIG. 4) and the second series of probes 66b (see FIG. 4). As shown in FIG. 10, the method 250 further comprises step 264 of removing the removable material 72 (see FIG. 4), if the removable material 72 is present in the thermochromatic witness assembly 64 (see FIG. 4).

Disclosed embodiments of the system 10 (see FIG. 4), the method 200 (see FIG. 9), and the method 250 (see FIG. 10) address a need to understand and control the thermal profile 62 (see FIG. 4) of a composite structure 28 (see FIG. 4), such as in the form of an aircraft composite part 28a (see FIG. 4) over a desired area. Moreover, the system 10 (see FIG. 4), the method 200 (see FIG. 9), and the method 250 (see FIG. 10) provide a system 10 and methods 200, 250 to map the thermal profile 62 (see FIG. 4) or thermal history of a composite structure 28 during the curing process and to streamline the thermal mapping composite fabrication process.

In addition, disclosed embodiments of the system 10 (see FIG. 4), the method 200 (see FIG. 9), and the method 250 (see FIG. 10) apply to repair processes for composite structures 28 (see FIG. 1), as well as manufacturing processes for composite structures 28 (see FIG. 1). Further, disclosed embodiments of the system 10 (see FIG. 4), the method 200 (see FIG. 9), and the method 250 (see FIG. 10) may reduce the cost and time to develop and manufacture composite structures 28 (see FIGS. 1, 4) and related tooling and curing processes, while optimizing composite structures 28 (see FIG. 1, 4), such as aircraft composite parts 28a, and design of the tool 90 (see FIG. 4).

In addition, disclosed embodiments of the system 10 (see FIG. 4), the method 200 (see FIG. 9), and the method 250 (see FIG. 10) may apply the thermochromatic material 68 (see FIG. 4) to a removable material 72, such as a peel ply 72a, a release film 72b (see FIG. 4), an FEP film 72c (see FIG. 4), or a caul plate 72d (see FIG. 4). Moreover, the thermochromatic material 68 (see FIG. 4) may be applied directly to developmental parts 92 (see FIG. 4) to quickly determine temperature profiles 94 (see FIG. 4) and to guide tool 90 (see FIG. 4) design. Further, the thermochromatic material 68 (see FIG. 4) may be applied directly to the surface 96 (see FIG. 4) of the tool 90 used for lay-up to verify tool heating during development and manufacture. The thermochromatic material 68 (see FIG. 4) may also be applied outside of aircraft composite part 28a (see FIGS. 1, 4) areas for in-process monitoring and validation of the cure cycle.

Figure 11:
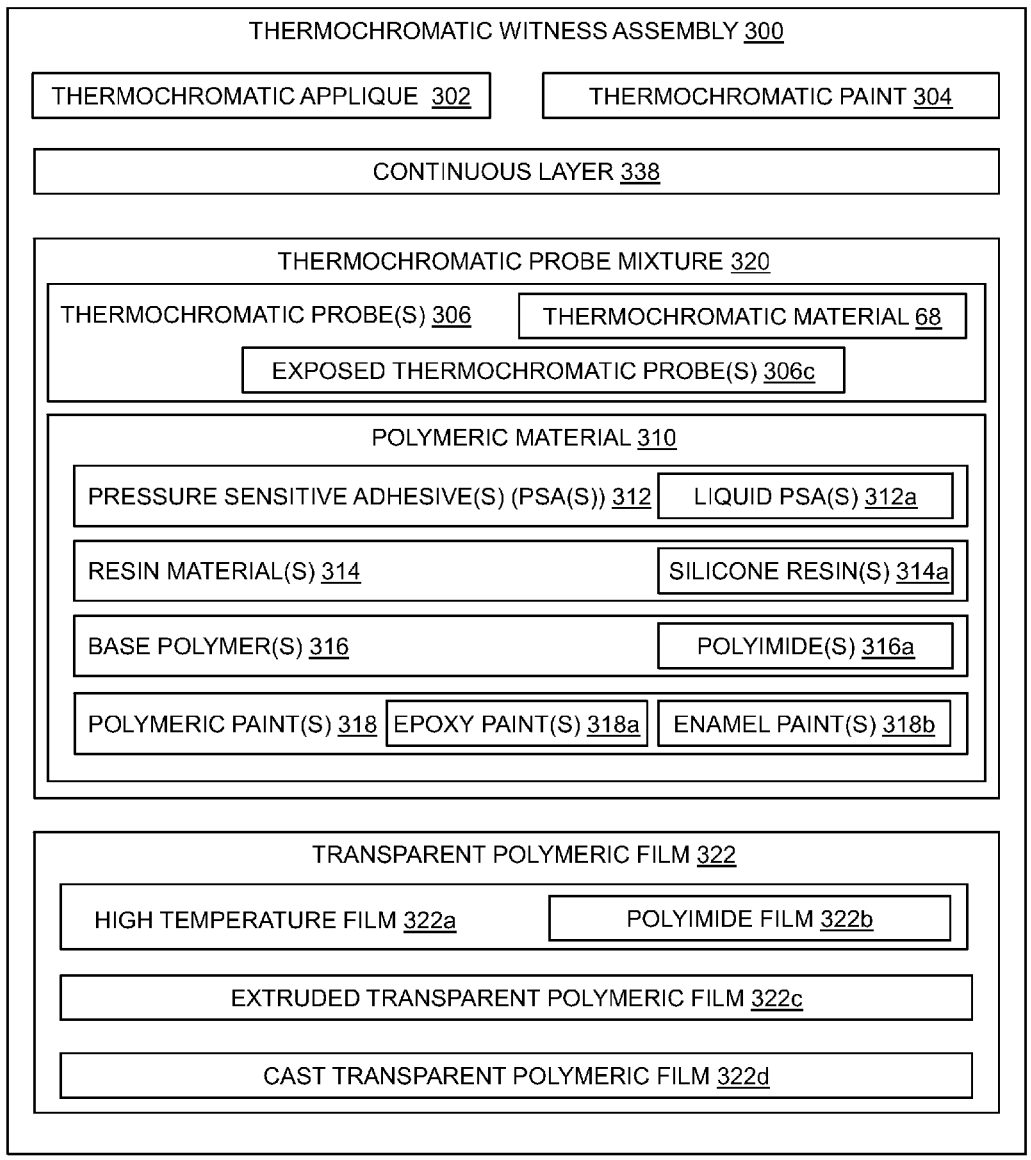
FIG. 11 is an illustration of a functional box diagram showing another embodiment of a thermochromatic witness assembly of the disclosure.
Figure 12:
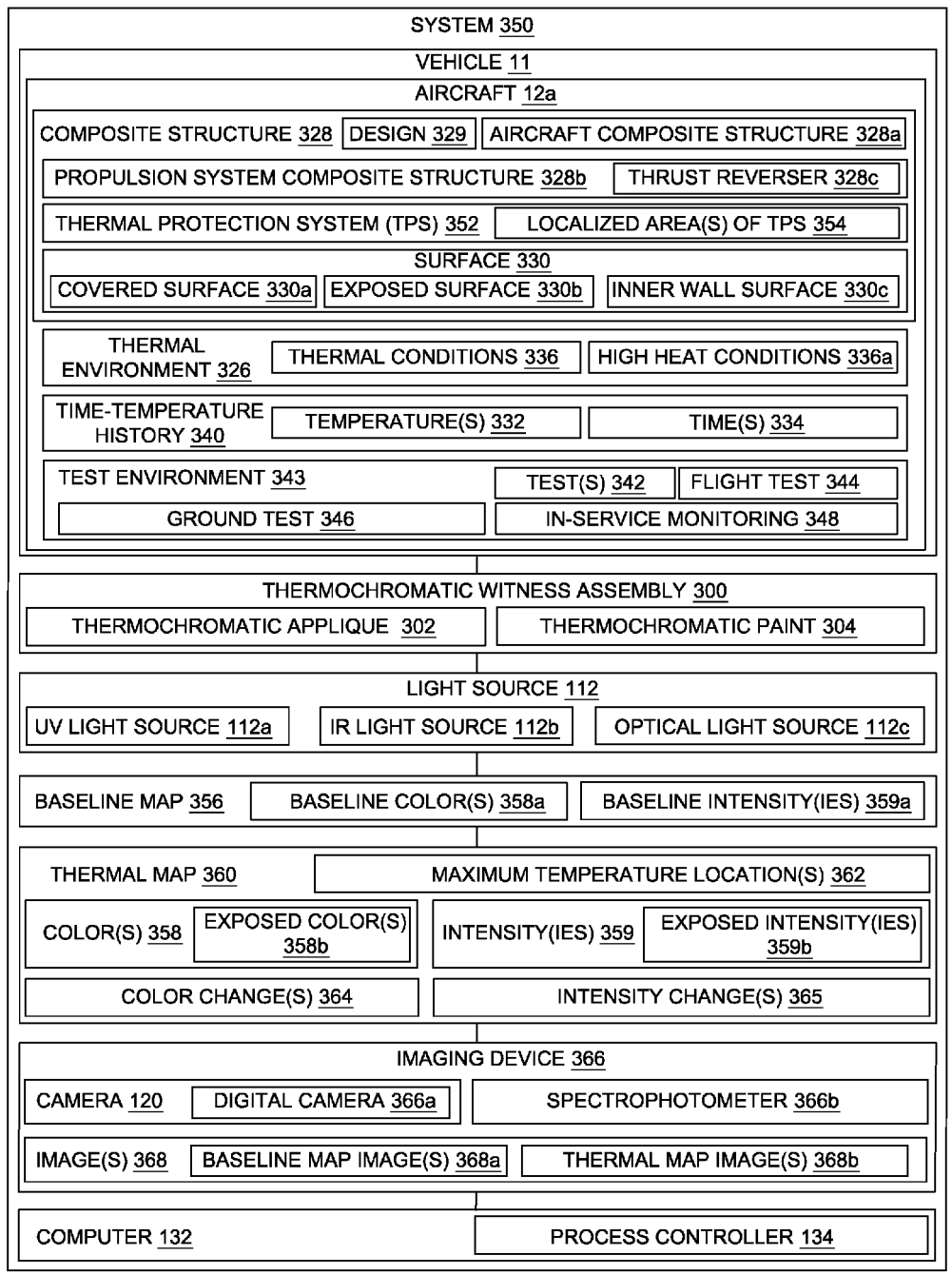
FIG. 12 is an illustration of a functional box diagram showing another embodiment of a system of the disclosure.

FIG. 11 is an illustration of a functional box diagram showing another embodiment of a thermochromatic witness assembly 300 of the disclosure. FIG. 12 is an illustration of a functional box diagram showing another embodiment of a system 350 of the disclosure, where the system 350 includes the thermochromatic witness assembly 300.

In one embodiment, there is provided the thermochromatic witness assembly 300 (see FIGS. 11, 12) for monitoring a thermal environment 326 (see FIG. 12) of a composite structure 328 (see FIGS. 1, 12). Preferably, the composite structure 328 (see FIGS. 1, 12) comprises an aircraft composite structure 328a (see FIGS. 1, 12).

Now referring to FIG. 11, the thermochromatic witness assembly 300 comprises a polymeric material 310 and one or more thermochromatic probes 306 mixed into the polymeric material 310 to form a thermochromatic probe mixture 320. Preferably a plurality of thermochromatic probes 306 (see FIG. 11) is mixed into the polymeric material 310 (see FIG. 11). The plurality of thermochromatic probes 306 (see FIG. 11) may, in one embodiment, comprise a first series of thermochromatic probes 306a (see FIG. 16A) and a second series of thermochromatic probes 306b (see FIG. 16A).

As shown in FIG. 11, the polymeric material 310 preferably comprises one or more of: pressure sensitive adhesives (PSAs) 312, including liquid PSAs 312a, acrylics, butyl rubber, ethylene-vinyl acetate, nitriles, natural rubber, silicone rubbers, hot melt adhesives, styrene block copolymers, or other suitable PSAs; resin materials 314, including silicone resins 314a, or other suitable resin materials; base polymers 316, including polyimides 316a, or other suitable base polymers; polymeric paints 318, including epoxy paints 318a, enamel paints 318b, or other suitable paints; or other suitable polymeric materials 310.

"One or more polymeric materials 310 (see FIG. 11)" may mean either, (a) only pressure sensitive adhesive(s) (PSA) 312 (see FIG. 11), only resin material(s) 314 (see FIG. 11), only base polymer(s) 316 (see FIG. 11), only polymeric paint(s) 316 (see FIG. 11), or only another suitable polymeric material 310 (see FIG. 11), or (b) any combination of pressure sensitive adhesive(s) (PSA) 312 (see FIG. 11), resin material(s) 314 (see FIG. 11), base polymer(s) 316 (see FIG. 11), polymeric paint(s) 316 (see FIG. 11), or other suitable polymeric materials 310 (see FIG. 11).

The one or more thermochromatic probes 306 (see FIG. 11) are preferably configured to sense one or more temperatures 332 (see FIG. 12), such as, for example, temperatures in a temperature range of −450° F. (minus four hundred fifty degrees Fahrenheit) to 800° F. (eight hundred degrees Fahrenheit). More preferably, the one or more thermochromatic probes 306 (see FIG. 11) are configured to sense one or more temperatures 332 (see FIG. 12), such as, for example, temperatures in a temperature range of −70° F. (minus seventy degrees Fahrenheit) to 500° F. (five hundred degrees Fahrenheit). Most preferably, the one or more thermochromatic probes 306 (see FIG. 11) are configured to sense one or more temperatures 332 (see FIG. 12), such as, for example, high temperatures in a temperature range of 250° F. (two hundred fifty degrees Fahrenheit) to 320° F. (three hundred twenty degrees Fahrenheit). In particular, the one or more thermochromatic probes 306 (see FIG. 11) are configured to sense temperatures 332 (see FIG. 12) and thermal conditions 336 in the thermal environment 326 (see FIG. 12). Preferably, the one or more thermochromatic probes 306 (see FIGS. 11, 12) are selected to sense the one or more temperatures 332 (see FIG. 12) in the thermal environment 326 (see FIG. 12) having high heat conditions 336a (see FIG. 12).

The one or more thermochromatic probes 306 (see FIG. 11) of the thermochromatic witness assembly 300 (see FIG. 11) comprise thermochromatic material 68 (see FIG. 11). As discussed above, the thermochromatic material 68 (see FIGS. 4, 11) may comprise thermochromatic probes or dyes tailored to activate at specific thermal or time-temperature ranges. When the thermochromatic material 68 (see FIG. 11) is activated by exposure to the temperatures 332 (see FIG. 12) to which it has been tailored, such as temperatures 332 (see FIG. 12) that are high and thermal conditions 336 (see FIG. 12) with high heat conditions 336a (see FIG. 12), the probe or dye undergoes fluorescent shifts, and exposed thermochromatic probes 306c (see FIG. 11) are obtained as a result. When illuminated by a light source 112 (see FIG. 12), discussed in further detail below, of a suitable wavelength, the fluorescent shifts in the thermochromatic material 68 (see FIG. 11) become visible, manifesting themselves as color change(s) 364 (see FIG. 11) and intensity change(s) 365 (see FIG. 12) in the color(s) 358 (see FIG. 12).

As shown in FIG. 11, the thermochromatic witness assembly 300 may preferably be in the form of a thermochromatic applique 302, or a thermochromatic paint 304. However, the thermochromatic witness assembly 300 may also be in another suitable form.

Figure 13:
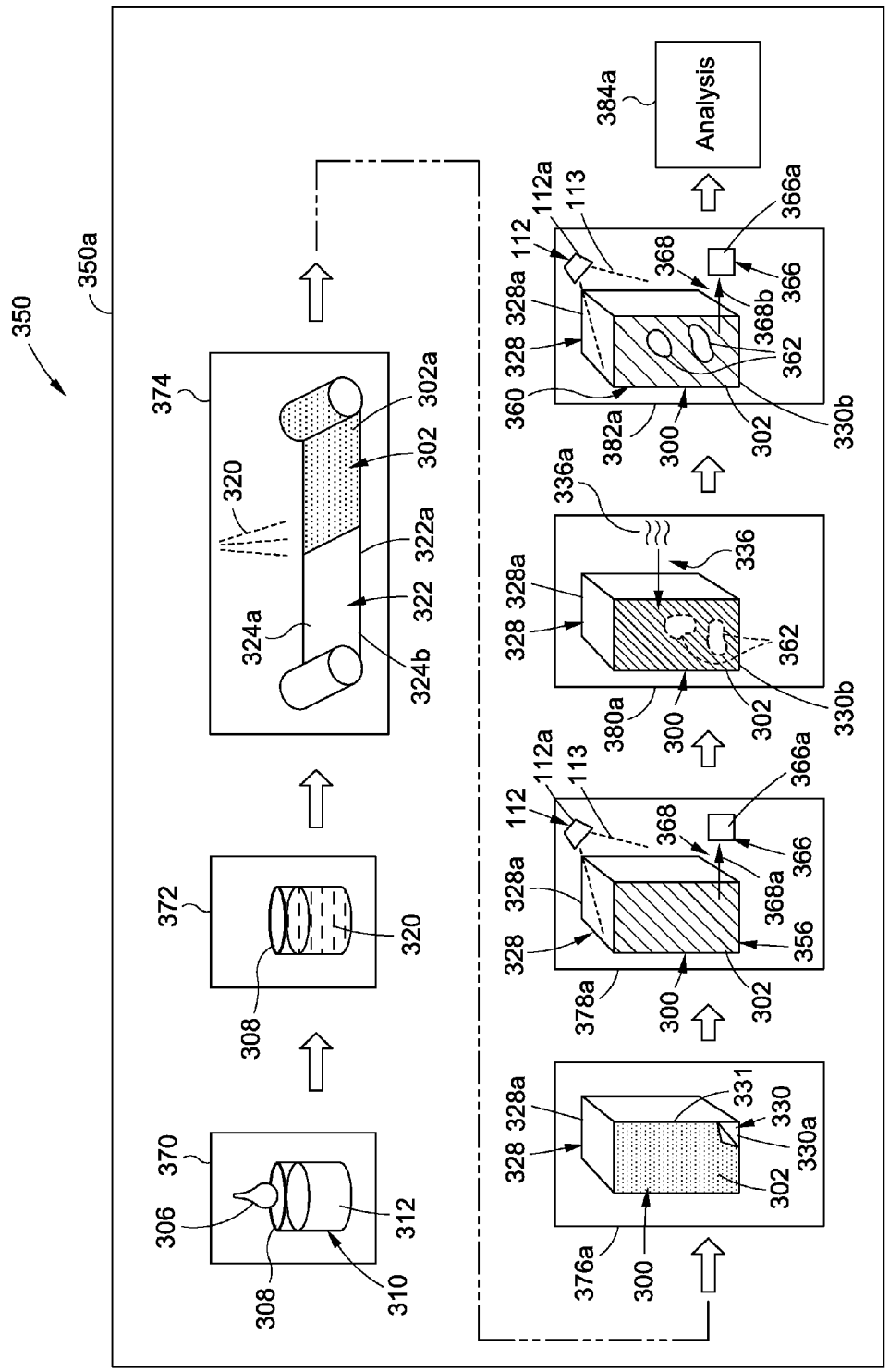
FIG. 13 is a diagrammatic representation of a schematic diagram of one embodiment of making and using a thermochromatic applique in an embodiment of the system of the disclosure.

In one embodiment of the thermochromatic applique 302 (see FIG. 11), such as thermochromatic applique 302a (see FIG. 13), the thermochromatic probe mixture 320 (see FIG. 11) may be applied to a transparent polymeric film 322 (see FIG. 11), thus forming the thermochromatic witness assembly 300 (see FIG. 11) in the form of the thermochromatic applique 302 (see FIG. 11). For example, as shown in FIG. 13, discussed in further detail below, in this embodiment, the one or more thermochromatic probes 306 are mixed into the polymeric material 310 comprising pressure sensitive adhesive (PSA) 312, such as liquid PSA 312a (see FIG. 11), to form the thermochromatic probe mixture 320. A continuous layer 338 (see FIG. 11) of the thermochromatic probe mixture 320 (see also FIG. 11) may be applied, such as by spraying or brushing, or another suitable application process, onto a first side 324a of the transparent polymeric film 322 (see also FIG. 11).

Figure 14:
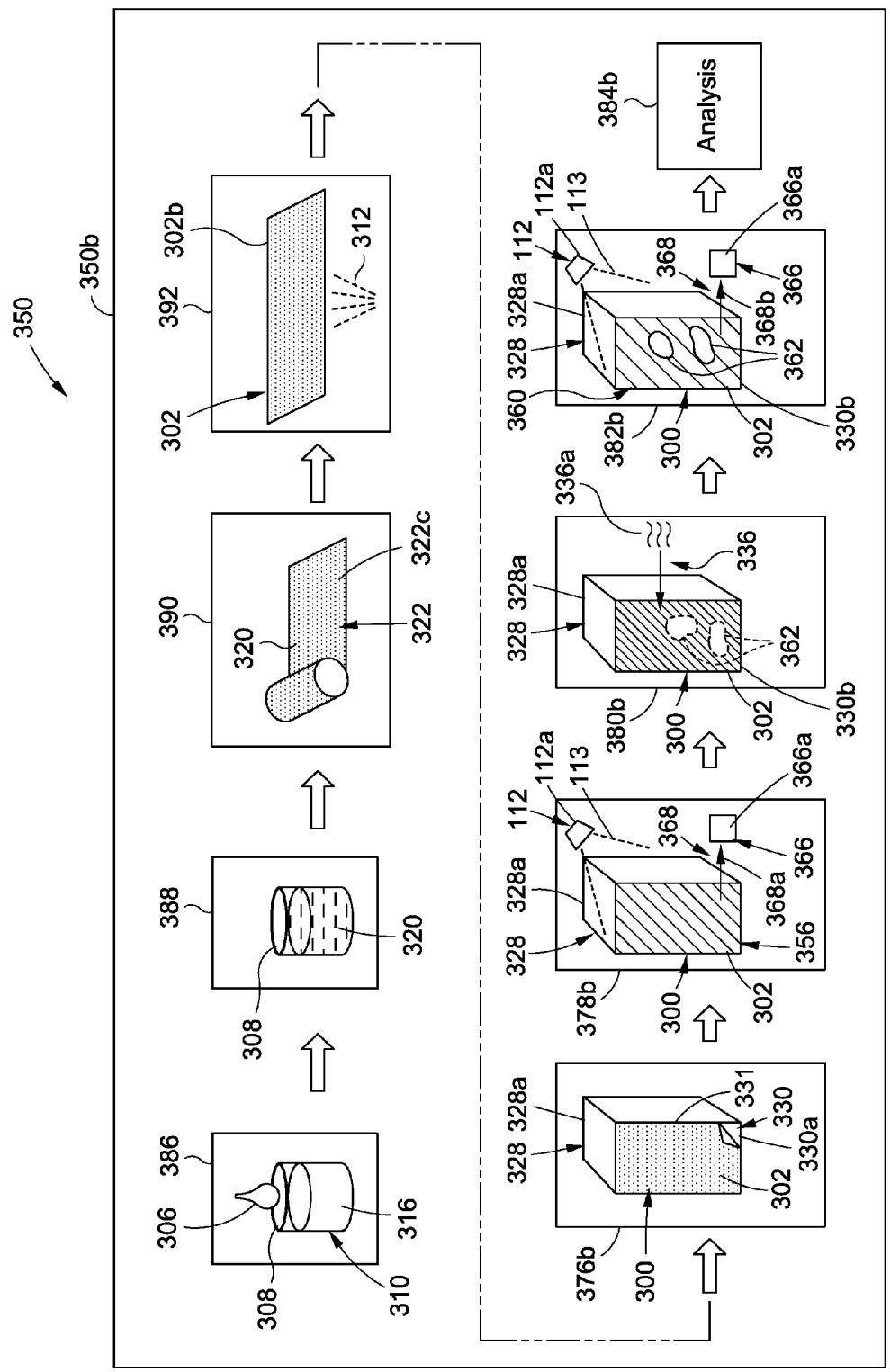
FIG. 14 is a diagrammatic representation of a schematic diagram of another embodiment of making and using a thermochromatic applique in another embodiment of the system of the disclosure.

In another embodiment of the thermochromatic applique 302 (see FIG. 11), such as thermochromatic applique 302b (see FIG. 14), the thermochromatic probe mixture 320 (see FIG. 11) may be formed into the transparent polymeric film 322 (see FIG. 11) with a pressure sensitive adhesive (PSA) 312 (see FIG. 11) applied thereto, thus forming the thermochromatic witness assembly 300 (see FIG. 11) in the form of the thermochromatic applique 302 (see FIG. 11). For example, as shown in FIG. 14, discussed in further detail below, in this embodiment, the one or more thermochromatic probes 306 are mixed into the polymeric material 310 comprising a base polymer 316, such as polyimide 316a (see FIG. 11), to form the thermochromatic probe mixture 320. The thermochromatic probe mixture 320 (see FIGS. 11, 14) is preferably formed into either an extruded transparent polymeric film 322c (see FIGS. 11, 14), or a cast transparent polymeric film 322d (see FIG. 11), with the pressure sensitive adhesive (PSA) 312 (see FIGS. 11, 14) applied to either the extruded transparent polymeric film 322c (see FIGS. 11, 14) or to the cast transparent polymeric film 322d (see FIG. 11).

The transparent polymeric film 322 (see FIG. 11) preferably remains stable across a wide range of temperatures, such as at temperatures in a temperature range of −450° F. (minus four hundred fifty degrees Fahrenheit) to 800° F. (eight hundred degrees Fahrenheit). More preferably, the transparent polymeric film 322 (see FIG. 11) remains stable at temperatures in a temperature range of −70° F. (minus seventy degrees Fahrenheit) to 500° F. (five hundred degrees Fahrenheit).

The transparent polymeric film 322 (see FIG. 11) of the thermochromatic applique 302 (see FIG. 11) is preferably a high temperature film 322a (see FIG. 11), such as a polyimide film 322b (see FIG. 11), for example, poly(4,4'-oxydiphenylene-pyromellitimide) KAPTON) (KAPTON is a registered trademark of E. I. Du Pont De Nemours and Company of Wilmington, Del.). Preferably, the transparent polymeric film 322 (see FIG. 11) is a high temperature film 322a (see FIG. 11) that is stable at high temperatures in a temperature range of 200° F. (two hundred degrees Fahrenheit) to 800° F. (eight hundred degrees Fahrenheit). More preferably, the transparent polymeric film 322 (see FIG. 11) is a high temperature film 322a (see FIG. 11) that is stable at high temperatures in a temperature range of 200° F. (two hundred fifty degrees Fahrenheit) to 500° F. (five hundred fifty-two degrees Fahrenheit). Most preferably, the transparent polymeric film 322 (see FIG. 11) is a high temperature film 322a (see FIG. 11) that is stable at high temperatures in a temperature range of 250° F. (two hundred fifty degrees Fahrenheit) to 320° F. (three hundred twenty degrees Fahrenheit).

In the embodiment where the thermochromatic witness assembly 300 (see FIG. 11) is in the form of a thermochromatic paint 304 (see FIG. 11), the one or more thermochromatic probes 306 (see FIG. 11) are preferably mixed into the polymeric material 310 (see FIG. 11) comprising polymeric paint 318 (see FIG. 11), such as epoxy paint 318a (see FIG. 11), enamel paint 318b (see FIG. 11), or another suitable polymeric paint 318, to form the thermochromatic probe mixture 320. The thermochromatic probe mixture 320 (see FIG. 11) is preferably applied directly and continuously to the surface 330 (see FIG. 12) of the composite structure 328 (see FIGS. 1, 12) and configured to monitor the thermal environment 326 (see FIG. 12) of the composite structure 328 (see FIGS. 1, 12). is formed from the one or more thermochromatic probes 306 mixed into polymeric paint 318.

The thermochromatic applique 302 (see FIG. 11) and the thermochromatic paint 304 (see FIG. 11) are configured to be applied directly and continuously to the surface 330 (see FIG. 12) of the composite structure 328 (see FIGS. 1, 12), to form a covered surface 330a (see FIG. 12) of the composite structure 328 (see FIG. 12). The thermochromatic applique 302 (see FIG. 11) and the thermochromatic paint 304 (see FIG. 11) are further configured to monitor the thermal environment 326 (see FIG. 12) of the composite structure 328 (see FIGS. 1, 12) by detecting one or more temperatures 332 (see FIG. 12) and one or more times 334 (see FIG. 12) an exposed surface 330b (see FIG. 12) of the composite structure 328 (see FIG. 12) is exposed to the thermal environment 326 (see FIG. 12), and in particular, is exposed to high heat conditions 336a (see FIG. 12) of the thermal environment 326 (see FIG. 12).

Now referring to FIG. 12, in another embodiment, there is provided the system 350 to monitor the thermal environment 326 of a composite structure 328 to facilitate optimization of a design 329 of the composite structure 328. Preferably, the composite structure 328 (see FIGS. 1, 12) is coupled to or housed within a vehicle 11 (see FIG. 12), such as an aircraft 12a (see FIGS. 1, 12). Preferably, the composite structure 328 (see FIGS. 1, 12) comprises an aircraft composite structure 328a (see FIGS. 1, 12), such as a propulsion system composite structure 328b (see FIG. 12), for example, a thrust reverser 328c (see FIG. 12), or another suitable aircraft composite structure 328a, or another suitable composite structure 328.

In use, aircraft composite structures 328a (see FIGS. 1, 12), such as propulsion system composite structures 328b (see FIG. 12), for example, thrust reversers 328c (see FIG. 12), are typically subjected to high heat conditions 336a (see FIG. 12) and temperatures 332 (see FIG. 12) that are very high, and are preferably used with a Thermal Protection System (TPS) 352 (see FIG. 12), such as in the form of insulation blankets or other suitable insulation devices or means. Use of the thermochromatic applique 302 (see FIG. 12) or the thermochromatic paint 304 (see FIG. 12) on the composite structure 328 (see FIGS. 1, 12), such as the aircraft composite structure 328a (see FIGS. 1, 12), for example, the propulsion system composite structure 328b (see FIG. 12), facilitates or allows for finding one or more localized areas 354 (see FIG. 12) of the TPS 352 (see FIG. 12), where the TPS 352 (see FIG. 12) may not be functioning properly or as designed. Such knowledge may then be used to produce a more robust TPS 352 (see FIG. 12).

As shown in FIG. 12, the system 350 comprises the thermochromatic witness assembly 300, as discussed in detail above. The thermochromatic witness assembly 300 (see FIGS. 11, 12) comprises the thermochromatic applique 302 (see FIGS. 11, 12), the thermochromatic paint 304 (see FIGS. 11, 12), or another suitable thermochromatic form or coating. Each of the thermochromatic applique 302 (see FIGS. 11, 12) and the thermochromatic paint 304 (see FIGS. 11, 12) comprises a plurality of thermochromatic probes 306 (see FIG. 11) mixed into the polymeric material 310 (see FIG. 11).

As discussed above, the polymeric material 310 (see FIG. 11) preferably comprises one or more of: pressure sensitive adhesives (PSAs) 312 (see FIG. 11), including liquid PSAs 312a (see FIG. 11), acrylics, butyl rubber, ethylene-vinyl acetate, nitriles, natural rubber, silicone rubbers, hot melt adhesives, styrene block copolymers, or other suitable PSAs; resin materials 314 (see FIG. 11), including silicone resins 314a (see FIG. 11), or other suitable resin materials; base polymers 316 (see FIG. 11), including polyimides 316a (see FIG. 11), or other suitable base polymers; polymeric paints 318 (see FIG. 11), including epoxy paints 318a (see FIG. 11), enamel paints 318b (see FIG. 11), or other suitable paints; or another suitable polymeric material 310.

In one embodiment, the thermochromatic applique 302 (see FIGS. 11-13), such as in the form of thermochromatic applique 302a (see FIG. 13), comprises the plurality of thermochromatic probes 306 (see FIG. 11) mixed into the PSA 312 (see FIG. 11), such as liquid PSA 312a (see FIG. 11), to form the thermochromatic probe mixture 320 (see FIG. 11) that is applied as a continuous layer 338 (see FIG. 11) onto the first side 324a (see FIG. 13) of the transparent polymeric film 322 (see FIGS. 11, 13).

In another embodiment, the thermochromatic applique 302 (see FIG. 11), such as in the form of thermochromatic applique 302b (see FIG. 14), comprises the plurality of thermochromatic probes 306 (see FIG. 11) mixed into a base polymer 316 (see FIG. 11), such as a polyimide 316a (see FIG. 11), to form the thermochromatic probe mixture 320 (see FIG. 11) that is formed into an extruded transparent polymeric film 322c (see FIGS. 11, 14), a cast transparent polymeric film 322d (see FIG. 11), or another type of transparent polymeric film 322. A pressure sensitive adhesive (PSA) 312 (see FIGS. 11, 14) is preferably applied to one side of the extruded transparent polymeric film 322c (see FIGS. 11, 14), to one side of the cast transparent polymeric film 322d (see FIG. 11), or to one side of another type of transparent polymeric film 322.

The thermochromatic witness assembly 300 (see FIGS. 11-13) is preferably applied to a surface 330 (see FIGS. 11-13) of the composite structure 328 (see FIGS. 11-13) to obtain a covered surface 330a (see FIGS. 11-13). The covered surface 330a (see FIGS. 11-13) is preferably exposed to thermal conditions 336 (see FIG. 12) during one or more tests 342 (see FIG. 12) performed in the thermal environment 326 (see FIG. 12) and in a test environment 343 (see FIG. 12), to obtain an exposed surface 330b (see FIGS. 11-13) having one or more maximum temperature locations 362 (see FIGS. 11-13). As shown in FIG. 12, the one or more tests 342 may comprise a flight test 344, a ground test 346, an in-service monitoring 348, or another suitable test performed on the composite structure 328, such as the aircraft composite structure 328a. The covered surface 330a (see FIG. 12) and the exposed surface 330b (see FIG. 12) may comprise an inner wall surface 330c (see FIG. 12) of the composite structure 328 (see FIG. 12), such as the aircraft composite structure 328a (see FIG. 12), for example, a thrust reverser 328c (see FIG. 12).

As shown in FIG. 12, the system 350 further comprises a light source 112 configured to fluoresce the plurality of thermochromatic probes 306 (see FIG. 11) of the covered surface 330a and of the exposed surface 330b The plurality of thermochromatic probes 306 (see FIG. 11) is preferably selected to sense one or more temperatures 332 (see FIG. 12) in the thermal environment 326 (see FIG. 12), and one or more times 334 (see FIG. 12) the exposed surface 330b (see FIG. 12) of the composite structure 328 (see FIG. 12) is exposed to the thermal environment 326 (see FIG. 12), and in particular, is exposed to high heat conditions 336a (see FIG. 12) of the thermal environment 326 (see FIG. 12).

As shown in FIG. 12, the light source 112 preferably comprises at least one of an ultraviolet (UV) light source 112a, an infrared (IR) light source 112b, an optical light source 112c, or another suitable light source 112. "At least one of" means either, (a) only an ultraviolet (UV) light source 112a (see FIG. 12), only an infrared (IR) light source 112b (see FIG. 12), only an optical light source 112c (see FIG. 12), or only another suitable light source 112, or (b) any combination of an ultraviolet (UV) light source 112a (see FIG. 12), an infrared (IR) light source 112b (see FIG. 12), an optical light source 112c (see FIG. 12), and/or another suitable light source 112.

The covered surface 330a (see FIG. 12) or the exposed surface 330b (see FIG. 12) may preferably be placed in close proximity to the light source 112 (see FIG. 12), so that the thermochromatic material 68 (see FIG. 1) of the thermochromatic witness assembly 300 (see FIGS. 11, 12) may be activated and fluoresced. The light source 112 (see FIG. 12) illuminates the thermochromatic material 68 (see FIG. 11) with illumination 113 (see FIGS. 13, 14, 17) of light of a preselected wavelength, such as in the ultraviolet (UV) light range (e.g., ultraviolet (UV) light having an electromagnetic radiation with a wavelength from 400 nm (nanometers) to 100 nm (nanometers)), or such as in the infrared (IR) light range (e.g., infrared (IR) light having an electromagnetic radiation with a wavelength from 700 nm (nanometers) to 1 mm (millimeter)), or of another suitable preselected wavelength.

The light source 112 (see FIG. 12) is configured to activate the thermochromatic material 68 (see FIG. 11) of the plurality of thermochromatic probes 306 (see FIG. 11) to prompt an onset of color changes 364 (see FIG. 12) in the thermochromatic material 68 (see FIG. 11). The color changes 364 (see FIG. 12) in the thermochromatic material 68 (see FIG. 11) are preferably used to determine one or more maximum temperature location(s) 362 (see FIG. 12) on the composite structure 328 (see FIG. 12), in order to map a time-temperature history 340 (see FIG. 12) of the composite structure 328 (see FIG. 12) during the one or more tests 342 (see FIG. 12) in the test environment 343 (see FIG. 12) and in the thermal environment 326 (see FIG. 12). The color changes 364 (see FIG. 12) may indicate that the composite structure 328 (see FIG. 12) has been subjected to temperatures 332 (see FIG. 12) outside the desired range of values. Thus, the thermochromatic material 68 (see FIG. 12) of the plurality of thermochromatic probes 306 (see FIG. 11) acts as a "witness" that indicates out-of-range temperatures 332 (see FIG. 12) that may be used to assess the suitability of the composite structure 328 (see FIG. 12).

As shown in FIG. 12, the system 350 further comprises an imaging device 366. The imaging device 366 (see FIG. 12) is configured to image and record, after application of the light source 112 (see FIG. 12), one or more images 368 (see FIG. 12) of the covered surface 330a (see FIG. 12) and one or more images 368 (see FIG. 12) of the exposed surface 330b (see FIG. 12). As further shown in FIG. 12, the imaging device 366 preferably comprises at least one of a camera 120, including a digital camera 366a; a spectrophotometer 366b, or another suitable imaging device 366. "At least one of" means either, (a) only a camera 120 (see FIG. 12), only a spectrophotometer 366b, or only another suitable imaging device 366, or (b) any combination of a camera 120 (see FIG. 12), a spectrophotometer 366b, and/or another suitable imaging device 366.

As shown in FIG. 12, the system 350 further comprises a baseline map 356 comprising one or more baseline colors 358a and one or more baseline intensities 359a. The baseline map 356 (see FIG. 12) is preferably obtained by applying the light source 112 (see FIG. 12) to the covered surface 330a (see FIG. 12), and imaging and recording the covered surface 330a (see FIG. 12) with the imaging device 366 (see FIG. 12). The imaging device 366 (see FIG. 12) is configured to image and record, after application of the light source 112 (see FIG. 12), one or more images 368 (see FIG. 12), such as one or more baseline map image(s) 368a (see FIG. 12) of the covered surface 330a (see FIG. 12).

As shown in FIG. 12, the system 350 further comprises one or more thermal maps 360. Each of the one or more thermal maps 360 (see FIG. 12) comprises one or more color(s) 358 (see FIG. 12), such as one or more exposed color(s) 358b (see FIG. 12), and one or more intensity(ies) 359 (see FIG. 12), such as one or more exposed intensity(ies) 359b (see FIG. 12). Each of the one or more thermal maps 360 (see FIG. 12) is preferably obtained by applying the light source 112 (see FIG. 12) to the exposed surface 330b (see FIG. 12) of the composite structure 328 (see FIG. 12) covered with the thermochromatic witness assembly 300 (see FIG. 12), and imaging the exposed surface 330b (see FIG. 12) with the imaging device 366 (see FIG. 12). The imaging device 366 (see FIG. 12) is configured to image and record, after application of the light source 112 (see FIG. 12), one or more images 368 (see FIG. 12), such as one or more thermal map image(s) 368b (see FIG. 12) of the exposed surface 330b (see FIG. 12).

As shown in FIG. 12, the system 350 further comprises the time-temperature history 340 of the composite structure 328, obtained by comparing color changes 364 between the one or more exposed colors 358b and the one or more baseline colors 358a, and by comparing intensity changes 365 between the one or more exposed intensities 359b and the one or more baseline intensities 359a. The comparisons in the color changes 364 between the one or more exposed colors 358b and the one or more baseline colors 358a, and the comparisons in the intensity changes 365 between the one or more exposed intensities 359b and the one or more baseline intensities 359a, may be compared and analyzed using a known image analysis computer software or program, or by human analysis. The color changes 364 (see FIG. 12) and the intensity changes 365 (see FIG. 12) preferably directly correlate to the temperature-time history 340 (see FIG. 12) across the composite structure 328 (see FIG. 12), preferably the aircraft composite structure 328a (see FIGS. 1, 12), such as in the form of the propulsion system composite structure 328b (see FIG. 12), for example, the thrust reverser 328c (see FIG. 12), and in particular, across an inner wall surface 330c (see FIG. 12). Such color changes 364 (see FIG. 12) and intensity changes 365 (see FIG. 12) may preferably be translated into one or more thermal maps 360 (see FIG. 12) that may be analyzed with the known image analysis computer software or program, or by human analysis. The results are preferably used to improve and/or validate the design 329 (see FIG. 12) of the composite structure 328 (see FIG. 12), such as the inner wall surface 330c (see FIG. 12) or a thermal insulation, in order to produce an optimal design of the Thermal Protection System (TPS) 352 (see FIG. 12).

The thermochromatic witness assembly 300 (see FIGS. 11, 12) monitors the thermal environment 326 (see FIG. 12) and maps the time-temperature history 340 (see FIG. 12) of the composite structure 328 (see FIG. 12), such as the aircraft composite structure 328a (see FIG. 12), that is exposed to high heat conditions 336a (see FIG. 12) during the one or more tests 342 (see FIG. 12), such as the flight test 344 (see FIG. 12), the ground test 346 (see FIG. 12), the in-service monitoring 348 (see FIG. 12), or another suitable test of the composite structure 328 (see FIG. 12), such as the aircraft composite structure 328a (see FIG. 12).

As shown in FIG. 12, the system 350 further comprises a computer 132 that may be used to store the one or more images 368 in a memory. Based on the one or more images 368 (see FIG. 12) recorded by the imaging device 366 (see FIG. 12), the computer 132 (see FIG. 12) may provide information to a process controller 134 (see FIG. 12) that may adjust process parameters, such as temperature(s) 332 (see FIG. 12), of the thermal environment 326 (see FIG. 12).

FIG. 13 is a diagrammatic representation of a schematic diagram of one embodiment of making and using a thermochromatic witness assembly 300, such as a thermochromatic applique 302, in the form of thermochromatic applique 302a, in an embodiment of the system 350, such as in the form of system 350a, of the disclosure. The system 350, such as in the form of system 350a, includes the thermochromatic witness assembly 300, such as the thermochromatic applique 302, in the form of thermochromatic applique 302a, and both are used to monitor the thermal environment 326 (see FIG. 12) of the composite structure 328 (see FIG. 12).

As shown in FIG. 13, in a probe/PSA mixing operation 370, one or more thermochromatic probes 306 are first mixed in a mixing vessel 308 with the polymeric material 310, such as in the form of a pressure sensitive adhesive (PSA) 312, to make the PSA 312 thermochromatic. Next, as further shown in FIG. 13, in a probe mixture forming operation 372, the thermochromatic probe mixture 320 is formed after the one or more thermochromatic probes 306 are sufficiently mixed in the mixing vessel 308 with the polymeric material 310, such as in the form of the pressure sensitive adhesive (PSA) 312.

Next, as further shown in FIG. 13, in a thermochromatic applique forming operation 374, the thermochromatic probe mixture 320 is applied to the transparent polymeric film 322 to form the thermochromatic applique 302, such as in the form of thermochromatic applique 302a. The transparent polymeric film 322 (see FIG. 13) preferably comprises a high temperature film 322a (see FIG. 13) and has a first side 324a (see FIG. 13) and a second side 324b (see FIG. 13). As shown in the thermochromatic applique forming operation 374 of FIG. 13, the thermochromatic probe mixture 320, comprising the one or more thermochromatic probes 306 and the pressure sensitive adhesive (PSA) 312, may be sprayed onto the first side 324a of the transparent polymeric film 322 to form the thermochromatic applique 302, such as in the form of thermochromatic applique 302a.

Next, as further shown in FIG. 13, in a thermochromatic applique application operation 376a, the thermochromatic witness assembly 300, such as in the form of the thermochromatic applique 302, is applied to the composite structure 328, such as an aircraft composite structure 328a, to obtain a thermochromatic coated structure 331. The thermochromatic witness assembly 300, such as in the form of the thermochromatic applique 302, is applied directly and continuously over and to the surface 330 of the composite structure 328 to obtain the covered surface 330a.

Next, as further shown in FIG. 13, in a baseline map operation 378a, a light source 112, such as an ultraviolet (UV) light source 112a, applies illumination 113 to the covered surface 330a of the composite structure 328, such as the aircraft composite structure 328a, to fluoresce the plurality of thermochromatic probes 306 (see the probe/PSA mixing operation 370), of the thermochromatic witness assembly 300, such as in the form of the thermochromatic applique 302, to obtain a baseline map 356. The baseline map 356 (see FIGS. 12, 13) comprises one or more baseline colors 358a (see FIG. 12) and one or more baseline intensities 359a (see FIG. 12).

In the baseline map operation 378a (see FIG. 13), images 368 (see FIG. 13), such as baseline map images 368a (see FIG. 13), of the one or more baseline colors 358a (see FIG. 12) and the one or more baseline intensities 359a (see FIG. 12), of the baseline map 356 (see FIG. 13), are imaged and recorded with the imaging device 366 (see FIG. 13), such as in the form of a digital camera 366a (see FIG. 13). Preferably, the images 368 (see FIG. 13) of the one or more baseline colors 358a (see FIG. 12) and the one or more baseline intensities 359a (see FIG. 12) of the baseline map 356 (see FIGS. 12, 13) are imaged using the imaging device 366 (see FIG. 13). The images 368 (see FIG. 13) are then stored in the computer 132 (see FIG. 12) or another suitable storage device or media.

Next, as further shown in FIG. 13, in a thermal environment exposure operation 380a, the covered surface 330a of the composite structure 328, such as in the form of the aircraft composite structure 328a, is exposed to thermal conditions 336 such as high heat conditions 336a, in the thermal environment 326 (see FIG. 12) during one or more tests 342 (see FIG. 12), to obtain an exposed surface 330b having one or more maximum temperature locations 362. The thermochromatic witness assembly 300 (see FIG. 13), such as in the form of the thermochromatic applique 302 (see FIG. 13), monitors the thermal environment 326 (see FIG. 12).

Next, as further shown in FIG. 13, in a thermal map operation 382a, the light source 112, such as the ultraviolet (UV) light source 112a, applies illumination 113 to the exposed surface 330b having the one or more maximum temperature locations 362, on the composite structure 328, such as the aircraft composite structure 328a. The light source 112 (see FIG. 13) fluoresces the plurality of exposed thermochromatic probes 306c (see FIG. 11) of the thermochromatic witness assembly 300 (see FIG. 13), such as in the form of the thermochromatic applique 302 (see FIG. 13), to obtain a thermal map 360 (see FIG. 13). The thermal map 360 (see FIGS. 12, 13) comprises one or more exposed colors 358b (see FIG. 12) and one or more exposed intensities 359b (see FIG. 12).

In the thermal map operation 382a (see FIG. 13), images 368 (see FIG. 13), such as thermal map images 368b (see FIG. 13), of the one or more exposed colors 358b (see FIG. 12) and the one or more exposed intensities 359b (see FIG. 12), of the thermal map 360 (see FIG. 13), are imaged and recorded with the imaging device 366 (see FIG. 13), such as in the form of digital camera 366a (see FIG. 13). Preferably, the images 368 (see FIG. 13) of the one or more exposed colors 358b (see FIG. 12) and the one or more exposed intensities 359b (see FIG. 12) of the thermal map 360 (see FIGS. 12, 13) are imaged using the imaging device 366 (see FIG. 13). The images 368 (see FIG. 13) are then stored in the computer 132 (see FIG. 12) or another suitable storage device or media.

Next, as further shown in FIG. 13, in an analysis operation 384a, color changes 364 (see FIG. 12) between the one or more exposed colors 358b (see FIG. 12) and the one or more baseline colors 358a (see FIG. 12) are compared, and intensity changes 365 (see FIG. 12) between the one or more exposed intensities 359b (see FIG. 12) and the one or more baseline intensities 359a (see FIG. 12) are compared, to obtain a time-temperature history 340 (see FIG. 12) of the composite structure 328 (see FIG. 13), such as the aircraft composite structure 328a (see FIG. 13). The time-temperature history 340 (see FIG. 12) is preferably used to facilitate optimization of the design 329 (see FIG. 12) of the composite structure 328 (see FIG. 13), such as the aircraft composite structure 328a (see FIG. 13).

FIG. 14 is a diagrammatic representation of a schematic diagram of another embodiment of making and using a thermochromatic witness assembly 300, such as a thermochromatic applique 302, in the form of thermochromatic applique 302b, in an embodiment of the system 350, such as in the form of system 350b, of the disclosure. The system 350, such as in the form of system 350b, includes the thermochromatic witness assembly 300, such as the thermochromatic applique 302, in the form of thermochromatic applique 302b, and both are used to monitor the thermal environment 326 (see FIG. 12) of the composite structure 328 (see FIGS. 12, 14).

As shown in FIG. 14, in a probe/base polymer mixing operation 386, one or more thermochromatic probes 306 are first mixed in the mixing vessel 308 with the polymeric material 310, such as in the form of a base polymer 316, to make the base polymer 316 thermochromatic. Next, as further shown in FIG. 14, in a probe mixture forming operation 388, the thermochromatic probe mixture 320 is formed after the one or more thermochromatic probes 306 are sufficiently mixed in the mixing vessel 308 with the polymeric material 310, such as in the form of the base polymer 316.

Next, as further shown in FIG. 14, in a film making operation 390, the thermochromatic probe mixture 320 is extruded or cast into the transparent polymeric film 322. FIG. 14 shows the transparent polymeric film 322 comprising an extruded transparent polymeric film 322c formed through a known extrusion process. Alternatively, the transparent polymeric film 322 comprises a cast transparent polymeric film 322d (see FIG. 11) formed through a known casting process, or another suitable transparent polymeric film 322 (see FIG. 11) formed via a known film forming process.

Next, as further shown in FIG. 14, in a PSA application and thermochromatic applique forming operation 392, a pressure sensitive adhesive (PSA) 312 is applied to one side of the transparent polymeric film 322 to form the thermochromatic applique 302, such as in the form of thermochromatic applique 302b.

Next, as further shown in FIG. 14, in a thermochromatic applique application operation 376b, the thermochromatic witness assembly 300, such as in the form of the thermochromatic applique 302, is applied to the composite structure 328, such as an aircraft composite structure 328a, to obtain a thermochromatic coated structure 331. The thermochromatic witness assembly 300, such as in the form of the thermochromatic applique 302, is applied directly and continuously over and to the surface 330 of the composite structure 328 to obtain the covered surface 330a.

Next, as further shown in FIG. 14, in a baseline map operation 378b, a light source 112, such as an ultraviolet (UV) light source 112a, applies illumination 113 to the covered surface 330a of the composite structure 328, such as the aircraft composite structure 328a, to fluoresce the plurality of thermochromatic probes 306 (see the probe/base polymer mixing operation 386), of the thermochromatic witness assembly 300, such as in the form of the thermochromatic applique 302, to obtain a baseline map 356. The baseline map 356 (see FIGS. 12, 14) comprises one or more baseline colors 358a (see FIG. 12) and one or more baseline intensities 359a (see FIG. 12).

In the baseline map operation 378b (see FIG. 14), images 368 (see FIG. 14), such as baseline map images 368a (see FIG. 14), of the one or more baseline colors 358a (see FIG. 12) and the one or more baseline intensities 359a (see FIG. 12), of the baseline map 356 (see FIG. 14), are imaged and recorded with the imaging device 366 (see FIG. 14), such as in the form of a digital camera 366a (see FIG. 14). Preferably, the images 368 (see FIG. 14) of the one or more baseline colors 358a (see FIG. 12) and the one or more baseline intensities 359a (see FIG. 12) of the baseline map 356 (see FIGS. 12, 14) are imaged using the imaging device 366 (see FIG. 14). The images 368 (see FIG. 14) are then stored in the computer 132 (see FIG. 12) or another suitable storage device or media.

Next, as further shown in FIG. 14, in a thermal environment exposure operation 380b, the covered surface 330a of the composite structure 328, such as in the form of the aircraft composite structure 328a, is exposed to thermal conditions 336, such as high heat conditions 336a, in the thermal environment 326 (see FIG. 12) during one or more tests 342 (see FIG. 12), to obtain an exposed surface 330b having one or more maximum temperature locations 362. The thermochromatic witness assembly 300 (see FIG. 14), such as in the form of the thermochromatic applique 302 (see FIG. 14), monitors the thermal environment 326 (see FIG. 12).

Next, as further shown in FIG. 14, in a thermal map operation 382b, the light source 112, such as the ultraviolet (UV) light source 112a, applies illumination 113 to the exposed surface 330b having the one or more maximum temperature locations 362, on the composite structure 328, such as the aircraft composite structure 328a. The light source 112 (see FIG. 14) fluoresces the plurality of exposed thermochromatic probes 306c (see FIG. 11) of the thermochromatic witness assembly 300 (see FIG. 14), such as in the form of the thermochromatic applique 302 (see FIG. 14), to obtain the thermal map 360 (see FIG. 14). The thermal map 360 (see FIGS. 12, 13) comprises one or more exposed colors 358b (see FIG. 12) and one or more exposed intensities 359b (see FIG. 12).

In the thermal map operation 382b (see FIG. 13), images 368 (see FIG. 13), such as thermal map images 368b (see FIG. 13), of the one or more exposed colors 358b (see FIG. 12) and the one or more exposed intensities 359b (see FIG. 12), of the thermal map 360 (see FIG. 14), are imaged and recorded with the imaging device 366 (see FIG. 14), such as in the form of digital camera 366a (see FIG. 14). Preferably, the images 368 (see FIG. 14) of the one or more exposed colors 358b (see FIG. 12) and the one or more exposed intensities 359b (see FIG. 12) of the thermal map 360 (see FIGS. 12, 14) are imaged using the imaging device 366 (see FIG. 14). The images 368 (see FIG. 14) are then stored in the computer 132 (see FIG. 12) or another suitable storage device or media.

Next, as further shown in FIG. 14, in an analysis operation 384b, color changes 364 (see FIG. 12) between the one or more exposed colors 358b (see FIG. 12) and the one or more baseline colors 358a (see FIG. 12) are compared, and intensity changes 365 (see FIG. 12) between the one or more exposed intensities 359b (see FIG. 12) and the one or more baseline intensities 359a (see FIG. 12) are compared, to obtain the time-temperature history 340 (see FIG. 12) of the composite structure 328 (see FIG. 14), such as the aircraft composite structure 328a (see FIG. 14). The time-temperature history 340 (see FIG. 12) is preferably used to facilitate optimization of the design 329 (see FIG. 12) of the composite structure 328 (see FIG. 14), such as the aircraft composite structure 328a (see FIG. 14).

Figure 15:
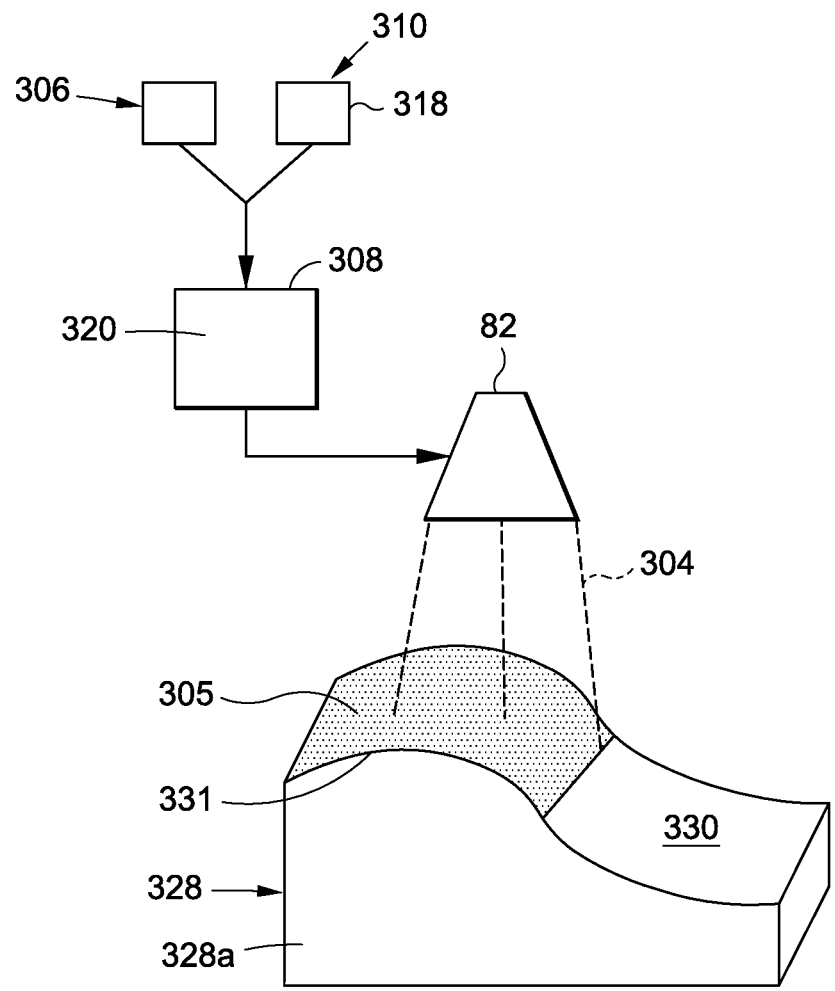
FIG. 15 is a diagrammatic representation of a schematic diagram of a thermochromatic paint sprayed onto a composite structure.

FIG. 15 is a diagrammatic representation of a schematic diagram of a thermochromatic paint 304 sprayed onto the composite structure 328, such as an aircraft composite structure 328a. As shown in FIG. 15, one or more thermochromatic probes 306 and the polymeric material 310, such as in the form of a polymeric paint 318, are mixed together in the mixing vessel 308 to form the thermochromatic probe mixture 320, in the form of thermochromatic paint 304. The thermochromatic probe mixture 320 (see FIG. 15), in the form of the thermochromatic paint 304 (see FIG. 15), may then be supplied and transferred to a sprayer apparatus 82 (see FIG. 15), or another suitable application apparatus, and sprayed or applied directly onto the surface 330 (see FIG. 15) of the composite structure 328 (see FIG. 15), such as the aircraft composite structure 328a (see FIG. 15), to form a thermochromatic paint coating 305 (see FIG. 15) and a thermochromatic coated structure 331 (see FIG. 15).

Figure 16A:
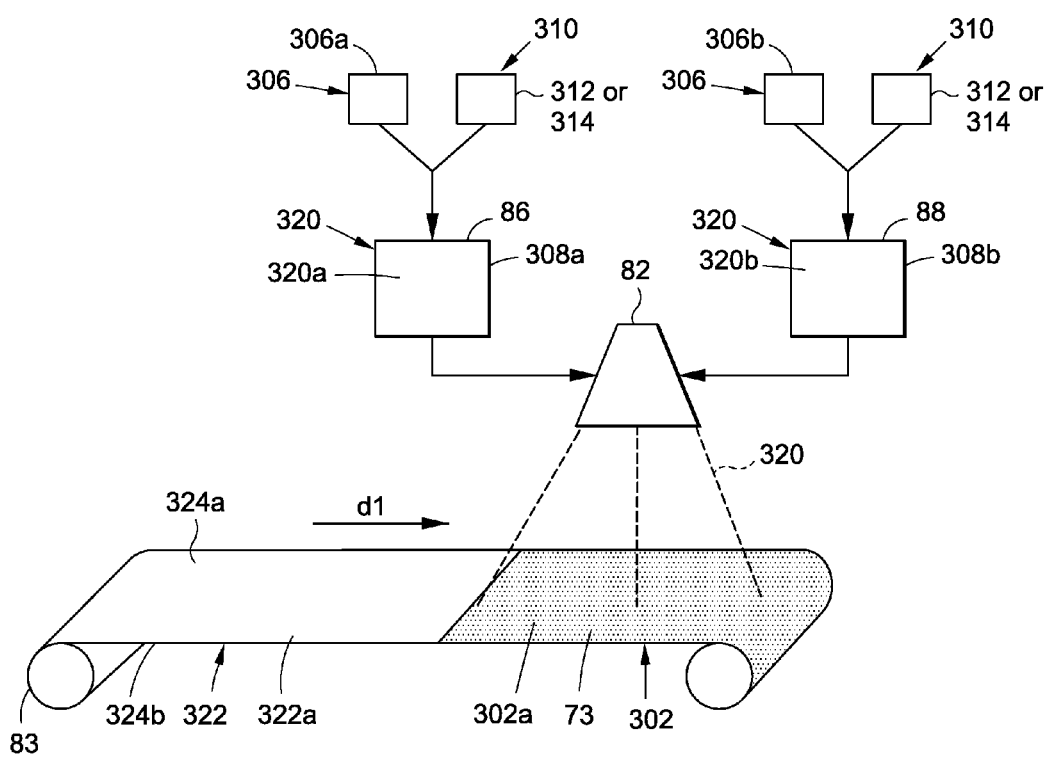
FIG. 16A is a diagrammatic representation of a schematic diagram of a thermochromatic applique formed from a first series of thermochromatic probes and a second series of thermochromatic probes.

FIG. 16A is a diagrammatic representation of a schematic diagram of a thermochromatic applique 302, such as in the form of thermochromatic applique 302a, formed from a first series of thermochromatic probes 306a and a second series of thermochromatic probes 306b. As shown in FIG. 16A, the first series of thermochromatic probes 306a of the plurality of thermochromatic probes 306, and the polymeric material 310, such as, for example, in the form of pressure sensitive adhesive (PSA) 312, or resin materials 314, are mixed together in a first mixing vessel 308a to form a first supply source 86 of the thermochromatic probe mixture 320, in the form of a first thermochromatic probe mixture 320a. As further shown in FIG. 16A, the second series of thermochromatic probes 306b of the plurality of thermochromatic probes 306, and the polymeric material 310, such as, for example, in the form of pressure sensitive adhesive (PSA) 312, or resin materials 314, are mixed together in a second mixing vessel 308b to form a second supply source 88 of the thermochromatic probe mixture 320, in the form of a second thermochromatic probe mixture 320b.

The first supply source 86 (see FIG. 16A) of the thermochromatic probe mixture 320a (see FIG. 16A) and the second supply source 88 (see FIG. 16A) of the thermochromatic probe mixture 320b (see FIG. 16A) may then be supplied and transferred to the sprayer apparatus 82 (see FIG. 16A), or another suitable application apparatus, and mixed together. The thermochromatic probe mixture 320 (see FIG. 16A) is sprayed or applied directly onto the first side 324a (see FIG. 16A) of the transparent polymeric film 322 (see FIG. 16A) to form the thermochromatic applique 302 (see FIG. 16A), such as in the form of thermochromatic applique 302a (see FIG. 16A). As shown in FIG. 16A, the transparent polymeric film 322, such as in the form of high temperature film 322a, may be formed in a roll attached to a roller apparatus 83, and rolled in a direction ($d_1$) toward the sprayer apparatus 82. The transparent polymeric film 322 (see FIG. 16A) coated with the thermochromatic probe mixture 320 (see FIG. 16A) may be configured to be removable and thus form a thermochromatic coated removable material 73 (see FIG. 16A).

Figure 16B:
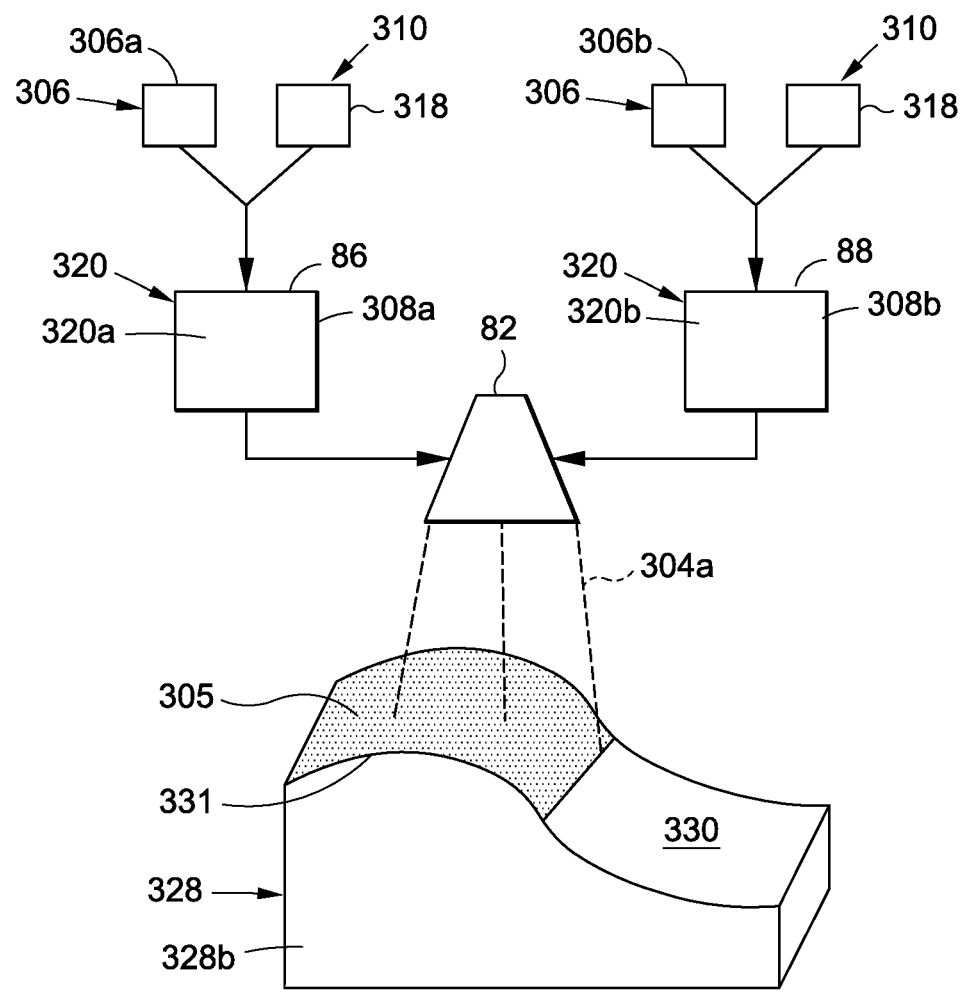
FIG. 16B is a diagrammatic representation of a schematic diagram of a thermochromatic paint formed from a first series of thermochromatic probes and a second series of thermochromatic probes.

FIG. 16B is a diagrammatic representation of a schematic diagram of a thermochromatic paint 304 formed from a first series of thermochromatic probes 306a and a second series of thermochromatic probes 306b. As shown in FIG. 16B, the first series of thermochromatic probes 306a of the plurality of thermochromatic probes 306 and the polymeric material 310, such as, for example, in the form of polymeric paint 318, are mixed together in the first mixing vessel 308a to form the first supply source 86 of the thermochromatic probe mixture 320, in the form of the first thermochromatic probe mixture 320a. As further shown in FIG. 16B, the second series of thermochromatic probes 306b of the plurality of thermochromatic probes 306 and the polymeric material 310, such as, for example, in the form of polymeric paint 318, are mixed together in the second mixing vessel 308b to form the second supply source 88 of the thermochromatic probe mixture 320, in the form of the second thermochromatic probe mixture 320b.

The first supply source 86 (see FIG. 16B) of the thermochromatic probe mixture 320a (see FIG. 16B) and the second supply source 88 (see FIG. 16B) of the thermochromatic probe mixture 320b (see FIG. 16B) may then be supplied and transferred to the sprayer apparatus 82 (see FIG. 16B), or another suitable application apparatus, and mixed together. The thermochromatic probe mixture 320 (see FIG. 16B), such as in the form of a thermochromatic paint mixture 304a (see FIG. 16B) may be sprayed or applied directly onto the surface 330 (see FIG. 16B) of the composite structure 328 (see FIG. 16B), such as the aircraft composite structure 328a (see FIG. 16B), to form a thermochromatic paint coating 305 (see FIG. 16B) and a thermochromatic coated structure 331 (see FIG. 16B).

Figure 17:
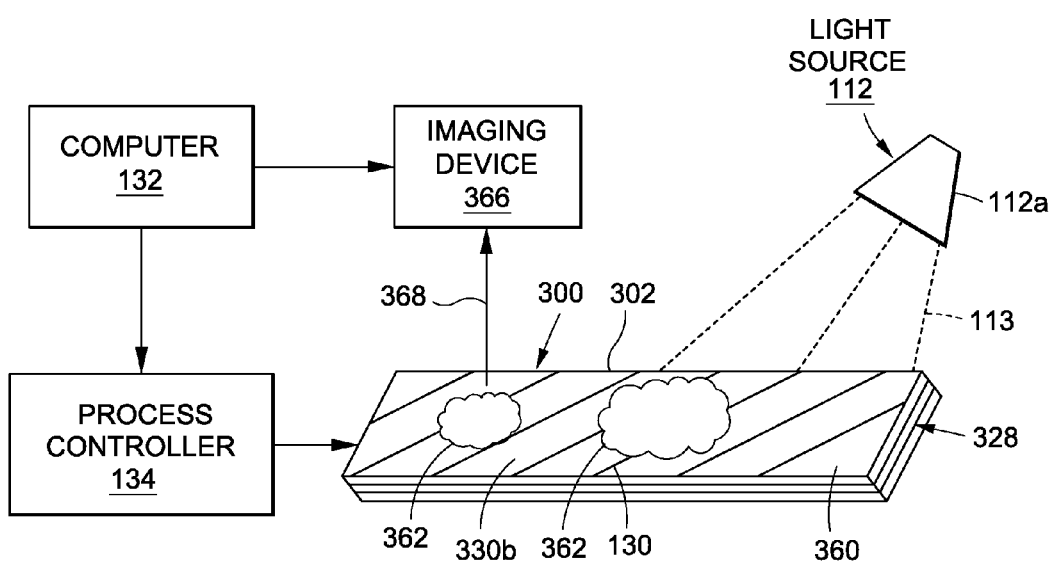
FIG. 17 is a diagrammatic representation of an embodiment of an exposed surface of a thermochromatic witness assembly showing maximum temperature locations illuminated by a light source.

FIG. 17 is a diagrammatic representation of an embodiment of an exposed surface 330b of a thermochromatic witness assembly 300, such as in the form of thermochromatic applique 302, showing maximum temperature locations 362 illuminated by the light source 112. FIG. 17 shows an activated thermochromatic material 130 illuminated by illumination 113 from the light source 112, such as ultraviolet (UV) light source 112a. The light source 112 may also comprise an infrared (IR) light source 112b (see FIG. 12), an optical light source 112c (see FIG. 12), or another suitable light source 112. The light source 112 (see FIG. 17) illuminates the thermochromatic material 68 (see FIG. 11) with illumination 113 (see FIG. 17) of light of a preselected wavelength, such as in the ultraviolet (UV) or infrared (IR) range, or another suitable wavelength of light.

As shown in FIG. 17, an imaging device 366 preferably images and records one or more images 368 of the thermal map 360, after activation with the light source 112. The imaging device 366 (see FIG. 17) may comprise a camera 120 (see FIG. 12), such as a digital camera 366a (see FIG. 12), a spectrophotometer (see FIG. 12), or another suitable imaging device. The activated thermochromatic material 130 (see FIG. 12) is preferably inspected under or in close proximity to the light source 112 (see FIG. 17) to inspect for maximum temperature locations 362 (see FIG. 12) on the composite structure 328 (see FIG. 17). Results of any maximum temperature locations 362 (see FIG. 12) and other thermal trends 128 (see FIG. 4) may be imaged or photographed with the imaging device 366 (see FIG. 17), recorded and documented.

As further shown in FIG. 17, a computer 132 may be used to store the one or more images 368 in a memory. Based on the one or more images 368 (see FIG. 17) imaged and recorded by the imaging device 366 (see FIG. 17), the computer 132 (see FIG. 17) may provide information to a process controller 134 (see FIG. 17).

Figure 18:
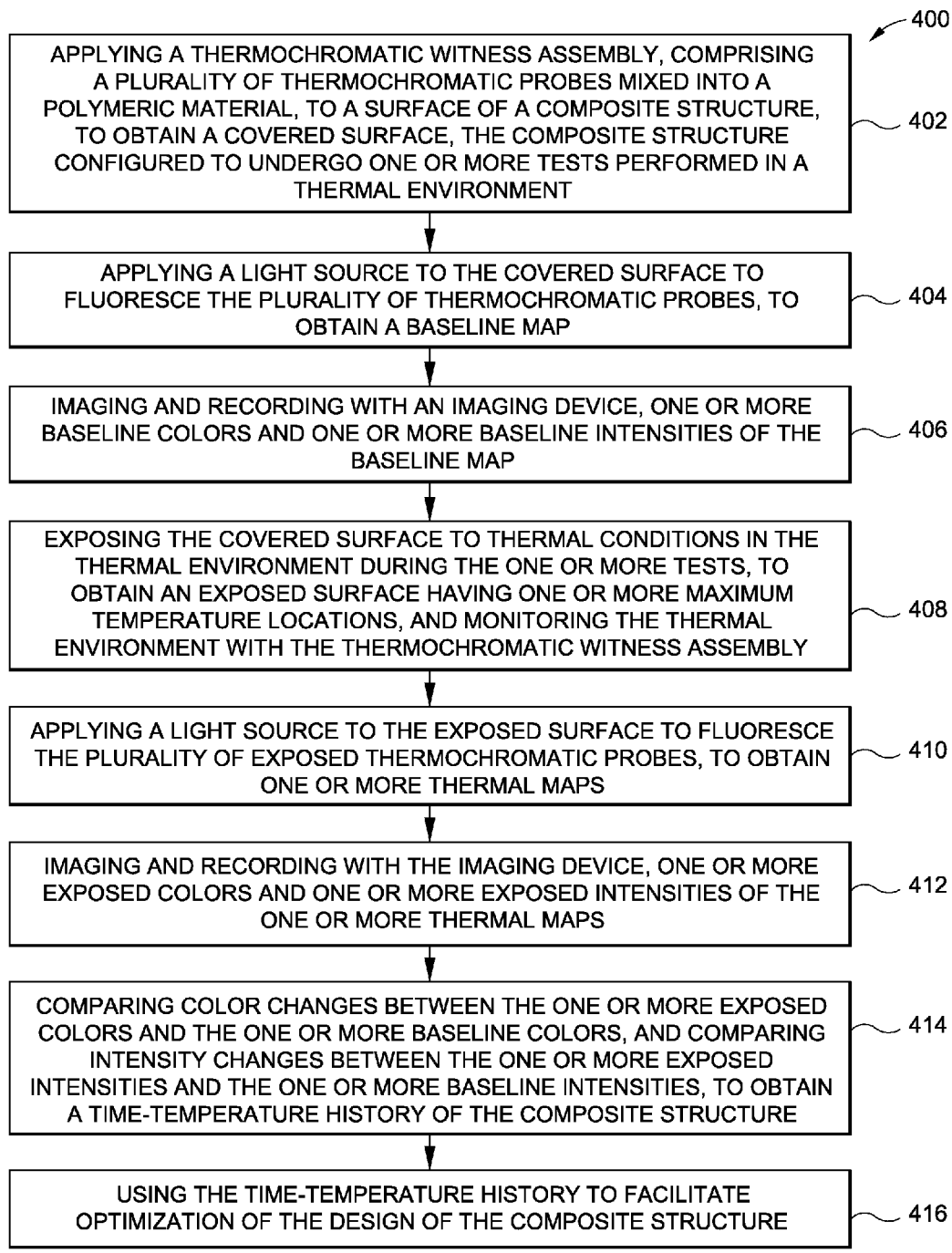
FIG. 18 is a flow diagram showing another embodiment of a method of the disclosure.

In another embodiment there is provided a method 400 (see FIG. 18) to monitor a thermal environment 326 (see FIG. 12) of a composite structure 328 (see FIGS. 1, 12) to facilitate optimization of a design 329 (see FIG. 12) of the composite structure 328 (see FIGS. 1, 12). FIG. 18 is a flow diagram showing the embodiment of the method 400 of the disclosure.

As shown in FIG. 18, the method 400 comprises step 402 of applying a thermochromatic witness assembly 300 (see FIG. 11), comprising a plurality of thermochromatic probes 306 (see FIG. 11) mixed into a polymeric material 310 (see FIG. 11), to a surface 330 (see FIGS. 12-14) of the composite structure 328 (see FIGS. 12-14), to obtain a covered surface 330*a* (see FIGS. 12-14). The composite structure 328 (see FIGS. 12-14) is preferably configured to undergo one or more tests 342 (see FIG. 12) performed in the thermal environment 326 (see FIG. 12).

The step 402 (see FIG. 18) of applying the thermochromatic witness assembly 300 (see FIG. 11) preferably comprises applying the thermochromatic witness assembly 300 (see FIG. 11) in a form of a thermochromatic applique 302 (see FIG. 11) or a thermochromatic paint 304 (see FIG. 11), directly and continuously to the surface 330 of the composite structure 328.

The step 402 (see FIG. 18) of applying the thermochromatic witness assembly 300 (see FIG. 11) preferably comprises applying the thermochromatic witness assembly 300 (see FIG. 11), comprising the plurality of thermochromatic probes 306 (see FIG. 11) mixed into the polymeric material 310 (see FIG. 11) to form a thermochromatic probe mixture 320 (see FIG. 11). In one embodiment, the thermochromatic probe mixture 320 (see FIGS. 11, 13) is applied to the transparent polymeric film 322 (see FIGS. 11, 13). In another embodiment, the thermochromatic probe mixture 320 (see FIGS. 11, 14) is formed into an extruded transparent polymeric film 322*c* (see FIGS. 11, 14) with a pressure sensitive adhesive (PSA) 312 (see FIGS. 11, 14) applied thereto, a cast transparent polymeric film 322*d* (see FIG. 11), with a pressure sensitive adhesive (PSA) 312 (see FIG. 11) applied thereto, or another suitable transparent polymeric film 322 (see FIG. 11) with a PSA 312 (see FIG. 11) applied thereto.

As shown in FIG. 18, the method 400 further comprises step 404 of applying a light source 112 (see FIGS. 12-14) to the covered surface 330*a* (see FIGS. 12-14) to fluoresce the plurality of thermochromatic probes 306 (see FIGS. 12-14), to obtain a baseline map 356 (see FIGS. 12-14) comprising one or more baseline colors 358*a* (see FIG. 12) and one or more baseline intensities 359*a* (see FIG. 12). The step 404 of applying the light source 112 (see FIGS. 12-14) to the covered surface 330*a* (see FIGS. 12-14) comprises applying the light source 112 (see FIGS. 12-14) preferably comprising at least one of an ultraviolet (UV) light source 112*a* (see FIG. 12), an infrared (IR) light source 112*b* (see FIG. 12), an optical light source 112*c* (see FIG. 12), or another suitable light source 112.

As shown in FIG. 18, the method 400 further comprises step 406 of imaging and recording with the imaging device 366 (see FIGS. 12-14), the one or more baseline colors 358*a* (see FIG. 12) and the one or more baseline intensities 359*a* (see FIG. 12) of the baseline map 356 (see FIGS. 12-14). The step 406 of imaging and recording with the imaging device 366 (see FIGS. 12-14) preferably comprises imaging and recording with the imaging device 366 (see FIGS. 12-14) comprising at least one of a camera 120 (see FIG. 12), including a digital camera 366*a* (see FIG. 12); a spectrophotometer 366*b* (see FIG. 12), or another suitable imaging device 366.

As shown in FIG. 18, the method 400 further comprises step 408 of exposing the covered surface 330*a* (see FIGS. 12-14) to thermal conditions 336 (see FIGS. 12-14) in the thermal environment 326 (see FIG. 12) during the one or more tests 342 (see FIG. 12), to obtain an exposed surface 330*b* (see FIGS. 12-14) having one or more maximum temperature locations 362 (see FIGS. 12-14, 17), and monitoring the thermal environment 326 (see FIG. 12) with the thermochromatic witness assembly 300 (see FIGS. 12-14). The step 408 of exposing the covered surface 330*a* (see FIGS. 12-14) to thermal conditions 336 (see FIG. 12) in the thermal environment 326 (see FIG. 12) during the one or more tests 342 (see FIG. 12) preferably comprises exposing the covered surface 330*a* (see FIGS. 12-14) to thermal conditions 336 (see FIG. 12) in the thermal environment 326 (see FIG. 12) during the one or more tests 342 (see FIG. 12) comprising a flight test 344 (see FIG. 12), a ground test 346 (see FIG. 12), in-service monitoring 348 (see FIG. 12) of the composite structure 328 (see FIGS. 12-14), or another suitable test 342 (see FIG. 12). The composite structure 328 (see FIGS. 12-14) preferably comprises an aircraft composite structure 328*a* (see FIGS. 12-14).

As shown in FIG. 18, the method 400 further comprises step 410 of applying the light source 112 (see FIGS. 12-14) to the exposed surface 330*b* (see FIGS. 12-14) to fluoresce the plurality of exposed thermochromatic probes 306*c* (see FIG. 11), to obtain one or more thermal maps 360 (see FIGS. 12-14), each comprising one or more exposed colors 358*b* (see FIG. 12) and one or more exposed intensities 359*b* (see FIG. 12). The step 410 of applying the light source 112 (see FIGS. 12-14) to the exposed surface 330*b* (see FIGS. 12-14) comprises applying the light source 112 (see FIGS. 12-14) preferably comprising at least one of an ultraviolet (UV) light source 112*a* (see FIG. 12), an infrared (IR) light source 112*b* (see FIG. 12), an optical light source 112*c* (see FIG. 12), or another suitable light source 112.

As shown in FIG. 18, the method 400 further comprises step 412 of imaging and recording with the imaging device 366 (see FIGS. 12-14), the one or more exposed colors 358*b* (see FIG. 12) and the one or more exposed intensities 359*b* (see FIG. 12) of the one or more thermal maps 360 (see FIGS. 12-14). The step 412 of imaging and recording with the imaging device 366 (see FIGS. 12-14) preferably comprises imaging and recording with the imaging device 366 (see FIGS. 12-14) comprising at least one of a camera 120 (see FIG. 12), including a digital camera 366*a* (see FIG. 12); a spectrophotometer 366*b* (see FIG. 12), or another suitable imaging device 366.

The surface colors 358 (see FIG. 12) and intensities 359 (see FIG. 12), such as the one or more exposed colors 358*b* (see FIG. 12) and the one or more exposed intensities 359*b* (see FIG. 12), respectively, of the one or more thermal maps 360 (see FIGS. 12-14) are preferably imaged and recorded with the imaging device 366 (see FIG. 12), such as the digital camera 366*a* (see FIG. 12) or the spectrophotometer 366*b* (see FIG. 12), and the light, digital camera, and/or spectrophotometer settings and locations are preferably repeated as close as possible to the light, digital camera, and/or spectrophotometer settings and locations used to obtain the baseline map 356, to ensure precision in the difference measurement. Typically, the thermochromatic applique 302 (see FIG. 12) or the thermochromatic paint 304 or coating may be a uniform color and intensity.

As shown in FIG. 18, the method 400 further comprises step 414 of comparing color changes 364 (see FIG. 12) between the one or more exposed colors 358*b* (see FIG. 12) and the one or more baseline colors 358*a* (see FIG. 12), and comparing intensity changes 365 (see FIG. 12) between the one or more exposed intensities 359*b* (see FIG. 12) and the one or more baseline intensities 359*a* (see FIG. 12), to obtain a time-temperature history 340 (see FIG. 12) of the composite structure 328 (see FIG. 12). As shown in FIG. 18, the method 400 further comprises step 416 of using the time-temperature history 340 (see FIG. 12) to facilitate optimization of the design 329 (see FIG. 12) of the composite structure 328 (see FIG. 12).

Use of the thermochromatic applique 302 (see FIG. 12) or the thermochromatic paint 304 (see FIG. 12) on the composite structure 328 (see FIGS. 1, 12), such as the aircraft composite structure 328*a* (see FIGS. 1, 12), for example, the propulsion system composite structure 328*b* (see FIG. 12), facilitates or allows for finding one or more localized areas 354 (see FIG. 12) of the Thermal Protection System (TPS) 352 (see FIG. 12), where the TPS 352 (see FIG. 12) may not be functioning properly, or as designed. Such knowledge may then be used to produce a more robust TPS 352 (see FIG. 12) before releasing a product with the composite structure 328 (see FIGS. 1, 12) into service.

Disclosed embodiments of the thermochromatic witness assembly 300 (see FIG. 11), system 350 (see FIG. 12), and method 400 (see FIG. 18) address a need to understand and control the time-temperature history 340 (see FIG. 12) of a surface 330 (see FIG. 12) of a composite structure 328 (see FIG. 12), such as an aircraft composite part 328*a* (see FIG. 12) in a thermal environment 326 (see FIG. 12). Moreover, the system 350 (see FIG. 12) and method 400 (see FIG. 18) using the thermochromatic witness assembly 300 (see FIG. 11) provide the ability to create a baseline map 356 (see FIG. 12) of the covered surface 330*a* (see FIG. 12). In addition, the system 350 (see FIG. 12) and method 400 (see FIG. 18) using the thermochromatic witness assembly 300 (see FIG. 11) provide the ability to create a thermal map 360 (see FIG. 12) of the exposed surface 330*b* (see FIG. 12) of the composite structure 328 (see FIG. 12) covered with the thermochromatic witness assembly 300 (see FIG. 11) during tests 342 (see FIG. 12) performed in the thermal environment 326 (see FIG. 12) and in the test environment 343 (see FIG. 12), for example, a flight test 344 (see FIG. 12), a ground test 346 (see FIG. 12), in-service monitoring 348 (see FIG. 12), or other suitable tests performed on the composite structure 328 (see FIG. 12), such as a propulsion system composite structure 328*b* (see FIG. 12). Preferably, the thermal environment 326 (see FIG. 12) is a high temperature environment, and the thermochromatic witness assembly 300 (see FIG. 11), such as in the form of a thermochromatic applique 302 (see FIG. 12) or a thermochromatic paint 304 (see FIG. 12), is applied to a composite structure 328 (see FIG. 12) subjected to high temperatures (e.g., 200° F. to 800° F.; or 200° F. to 500° F.).

Moreover, the thermochromatic witness assembly 300 (see FIG. 11), system 350 (see FIG. 12), and method 400 (see FIG. 18) provide a system 350 (see FIG. 12) and method 400 (see FIG. 18) using the thermochromatic witness assembly 300 (see FIG. 11), where a plurality of thermochromatic probes 306 (see FIG. 11) are mixed with or formed into a polymeric material 310 (see FIG. 11), such as a pressure sensitive adhesive (PSA) 312 (see FIG. 11), and applied to or formed into a transparent polymeric film 322 (see FIG. 11), such as a high temperature polyimide film that remains stable across a wide range of temperatures, for example, preferably a temperature range of −450° F. to 800° F., and more preferably a temperature range of −70° F. to 500° F. Preferably, the plurality of thermochromatic probes 306 (see FIG. 11) are selected that sense high temperature environments in a range needed for flight tests 344 (see FIG. 12), ground tests 346 (see FIG. 12), and in-service monitoring 348 (see FIG. 12) of inner wall surfaces 330*c* (see FIG. 12) of propulsion system composite structures 328*b* (see FIG. 12), such as thrust reversers 328*c* (see FIG. 12), with the needed reaction rates and activation longevity.

Further, the thermochromatic witness assembly 300 (see FIG. 11), system 350 (see FIG. 12), and method 400 (see FIG. 18) provide a system 350 (see FIG. 12) and method 400 (see FIG. 18) using the thermochromatic witness assembly 300 (see FIG. 11), where the thermochromatic applique 302 (see FIG. 12) or thermochromatic paint 304 (see FIG. 12) are applied to the entire surface 330 (see FIG. 12) of the composite structure 328 (see FIG. 12), such as the entire inner wall surface 330*c* (see FIG. 12), of the propulsion system composite structure 328*b* (see FIG. 12), such as the thrust reverser 328*c* (see FIG. 12), that help detect the temperature 332 (see FIG. 12) and time 334 (see FIG. 12) the surface 330 (see FIG. 12), such as the inner wall surface 330*c* (see FIG. 12), is exposed for. Use of a continuous thermochromatic applique 302 (see FIG. 12) or continuous thermochromatic paint 304 (see FIG. 12) or coating allows for finding one or more localized areas 354 (see FIG. 12) of a Thermal Protection System (TPS) 352 (see FIG. 12), where the TPS 352 (see FIG. 12) is not functioning properly or is not functioning as designed.

In addition, the thermochromatic witness assembly 300 (see FIG. 11), system 350 (see FIG. 12), and method 400 (see FIG. 18) enable designers and engineers to focus on and mitigate the maximum temperature locations 362 (see FIG. 12) (i.e., hotter areas) on the inner wall surface 330*c* (see FIG. 12) with the best design of the Thermal Protection System (TPS) 352 (see FIG. 12). Such knowledge may then be used to produce a more robust TPS 352 (see FIG. 12) before releasing the product into service. Further, the thermochromatic applique 302 (see FIG. 12) or thermochromatic paint 304 (see FIG. 12) or coating may be applied to in-service aircraft, on the thrust reverser inner wall or other high heat areas, for monitoring of the TPS 352 (see FIG. 12), or system as a whole.

Further, the thermochromatic witness assembly 300 (see FIG. 11), system 350 (see FIG. 12), and method 400 (see FIG. 18) provide a system and method using the thermochromatic witness assembly 300 (see FIG. 11) to observe and analyze color changes 364 (see FIG. 12) and intensity changes 365 (see FIG. 12) that directly correlate to the time-temperature history 340 (see FIG. 12) across the exposed surface 330*b* (see FIG. 12) of the composite structure 328 (see FIG. 12), such as the aircraft composite structure 328*a* (see FIG. 12), and may be translated into thermal maps 360 (see FIG. 12) that can be analyzed by designers, engineers, or others. The results may be used to improve and/or validate the design 329 (see FIG. 12) of the composite structure 328 (see FIG. 12), the inner wall surface 330*c* (see FIG. 12), the thermal insulation, or other design features in order to produce an optimal design. The thermochromatic witness assembly 300 (see FIG. 11), system 350 (see FIG. 12), and method 400 (see FIG. 18) may provide improved or better performance data, quicker turnaround of results, decreased costs and test times due to decreased or non-use of thermocouples to measure temperatures at various locations during flight tests, ground tests or in-service monitoring.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A thermochromatic applique to monitor a thermal environment of a composite structure, the thermochromatic applique comprising:
    a polymeric material selected from the group consisting of pressure sensitive adhesives (PSAs), including liquid PSAs; resin materials, including silicone resins; base polymers, including polyimides; and polymeric paints, including epoxy paints and enamel paints; and,
    one or more thermochromatic probes mixed into the polymeric material to form a thermochromatic probe mixture, the thermochromatic probe mixture applied to a removable transparent polymeric film, or formed into the removable transparent polymeric film with a pressure sensitive adhesive (PSA) applied thereto, to form the thermochromatic applique,
    the thermochromatic applique configured to be applied directly and continuously to and removed from a surface of the composite structure, and configured to monitor the thermal environment of the composite structure during a time the thermochromatic applique is applied to the surface of the composite structure, by detecting one or more temperatures and one or more times the surface of the composite structure is exposed to the thermal environment.

2. The thermochromatic applique of claim 1 wherein the the one or more thermochromatic probes comprise a first series of thermochromatic probes and a second series of thermochromatic probes.

3. The thermochromatic applique of claim 1 wherein the polymeric material is liquid PSA, and a continuous layer of the thermochromatic probe mixture is sprayed or brushed onto a first side of the removable transparent polymeric film.

4. The thermochromatic applique of claim 1 wherein the polymeric material is polyimide, and the thermochromatic probe mixture is formed into either an extruded removable transparent polymeric film or a cast removable transparent polymeric film, with the pressure sensitive adhesive (PSA) applied to either the extruded removable transparent polymeric film or the cast removable transparent polymeric film.

5. The thermochromatic applique of claim 1 wherein the removable transparent polymeric film comprises a polyimide film.

6. The thermochromatic applique of claim 1 wherein the removable transparent polymeric film is a high temperature film that is stable at a temperature range of 200° F. (two hundred degrees Fahrenheit) to 500° F. (five hundred degrees Fahrenheit).

7. The thermochromatic applique of claim 1 wherein the one or more thermochromatic probes are selected to sense the one or more temperatures in the thermal environment having high heat conditions.

8. The thermochromatic applique claim 1 wherein the composite structure comprises an aircraft composite structure, and the thermochromatic applique monitors the thermal environment during the time the thermochromatic applique is applied to the surface of the composite structure, and maps a time-temperature history of the aircraft composite structure that is exposed to high heat conditions during a flight test, a ground test, or in-service monitoring of the aircraft composite structure.

9. A system to monitor a thermal environment of a composite structure to facilitate optimization of a design of the composite structure, the system comprising:
    a thermochromatic applique comprising:
        a polymeric material selected from the group consisting of pressure sensitive adhesives (PSAs), including liquid PSAs; resin materials, including silicone resins; base polymers, including polyimides; and polymeric paints, including epoxy paints and enamel paints; and
        a plurality of thermochromatic probes mixed into the polymeric material to form a thermochromatic probe mixture, the thermochromatic probe mixture applied to a removable transparent polymeric film, or formed into the removable transparent polymeric film with a pressure sensitive adhesive (PSA) applied thereto to form the thermochromatic applique, the thermochromatic applique applied directly and continuously to a surface of the composite structure to obtain a covered surface, and the thermochromatic applique monitoring the thermal environment of the composite structure during a time the thermochromatic applique is applied to the surface of the composite structure, by detecting one or more temperatures and one or more times the covered surface of the composite structure is exposed to thermal conditions during one or more tests performed in the thermal environment, to obtain an exposed surface having one or more maximum temperature locations;
    a light source configured to fluoresce the plurality of thermochromatic probes of the covered surface and the exposed surface, the plurality of thermochromatic probes selected to sense one or more temperatures in the thermal environment;
    an imaging device configured to image and record one or more images of the covered surface and the exposed surface, after application of the light source;
    a baseline map comprising one or more baseline colors and one or more baseline intensities, obtained by applying the light source to the covered surface and imaging the covered surface;
    one or more thermal maps each comprising one or more exposed colors and one or more exposed intensities, and each obtained by applying the light source to the exposed surface and imaging the exposed surface; and
    a time-temperature history of the composite structure, obtained by comparing color changes between the one or more exposed colors and the one or more baseline colors, and by comparing intensity changes between the one or more exposed intensities and the one or more baseline intensities.

10. The system of claim 9 wherein the plurality of thermochromatic probes comprise a first series of thermochromatic probes and a second series of thermochromatic probes.

11. The system of claim 9 wherein the thermochromatic applique comprises the plurality of thermochromatic probes mixed into a liquid PSA to form the thermochromatic probe mixture that is applied as a continuous layer onto a first side of the removable transparent polymeric film.

12. The system of claim 9 wherein the thermochromatic applique comprises the plurality of thermochromatic probes mixed into a polyimide to form the thermochromatic probe mixture that is formed into either an extruded removable transparent polymeric film or a cast removable transparent polymeric film, with a pressure sensitive adhesive (PSA) applied to the extruded removable transparent polymeric film or to the cast removable transparent polymeric film.

13. The system of claim 9 wherein the light source comprises at least one of an ultraviolet (UV) light source, an infrared (IR) light source, or an optical light source.

14. The system of claim 9 wherein the imaging device comprises at least one of a camera, including a digital camera; or a spectrophotometer.

15. The system of claim 9 wherein the composite structure comprises an aircraft composite structure, and the thermochromatic applique monitors the thermal environment during the time the thermochromatic applique is applied to the surface of the composite structure, and maps the time-temperature history of the composite structure that is exposed to high heat conditions during one or more tests comprising a flight test, a ground test, or in-service monitoring of the composite structure.

16. A method to monitor a thermal environment of a composite structure to facilitate optimization of a design of the composite structure, the method comprising the steps of:
    applying a thermochromatic applique, comprising:
        a polymeric material selected from the group consisting of pressure sensitive adhesives (PSAs), including liquid PSAs; resin materials, including silicone resins; base polymers, including polyimides; and polymeric paints, including epoxy paints and enamel paints; and
        a plurality of thermochromatic probes mixed into the polymeric material to form a thermochromatic probe mixture, the thermochromatic probe mixture applied to a removable transparent polymeric film, or formed into the removable transparent polymeric film with a pressure sensitive adhesive (PSA) applied thereto to form the thermochromatic applique, the thermochromatic applique applied directly and continuously to a surface of the composite structure, to obtain a covered surface, the composite structure configured to undergo one or more tests performed in the thermal environment;
    applying a light source to the covered surface to fluoresce the plurality of thermochromatic probes, to obtain a baseline map comprising one or more baseline colors and one or more baseline intensities;
    imaging and recording with an imaging device, the one or more baseline colors and the one or more baseline intensities of the baseline map;
    exposing the covered surface to thermal conditions in the thermal environment during the one or more tests, to obtain an exposed surface having one or more maximum temperature locations, and monitoring the thermal environment with the thermochromatic applique during a time the thermochromatic applique is applied to the surface of the composite structure, by detecting one or more temperatures and one or more times the covered surface of the composite structure is exposed to the thermal conditions;
    applying the light source to the exposed surface to fluoresce the plurality of exposed thermochromatic probes, to obtain one or more thermal maps each comprising one or more exposed colors and one or more exposed intensities;
    imaging and recording with the imaging device, the one or more exposed colors and the one or more exposed intensities of the one or more thermal maps;
    comparing color changes between the one or more exposed colors and the one or more baseline colors, and comparing intensity changes between the one or more exposed intensities and the one or more baseline intensities, to obtain a time-temperature history of the composite structure; and
    using the time-temperature history to facilitate optimization of the design of the composite structure.

17. The method of claim 16 wherein the step of applying the thermochromatic applique comprises applying the thermochromatic applique directly and continuously to the surface of the composite structure, wherein the plurality of thermochromatic probes comprise a first series of thermochromatic probes and a second series of thermochromatic probes.

18. The method of claim 16 wherein the step of applying the thermochromatic applique comprises applying the thermochromatic applique comprising the plurality of thermochromatic probes mixed into the polymeric material to form the thermochromatic probe mixture, the thermochromatic probe mixture applied to the removable transparent polymeric film, or formed into either an extruded removable transparent polymeric film or a cast removable transparent polymeric film, with the pressure sensitive adhesive (PSA) applied thereto.

19. The method of claim 16 wherein the steps of applying the light source to the covered surface and to the exposed surface comprise applying the light source comprising at least one of an ultraviolet (UV) light source, an infrared (IR) light source, or an optical light source.

20. The method of claim 16 wherein the step of exposing the covered surface to thermal conditions in the thermal environment during the one or more tests comprises exposing the covered surface to thermal conditions in the thermal environment during the one or more tests comprising a flight test, a ground test, or in-service monitoring of the composite structure, the composite structure comprising an aircraft composite structure.

* * * * *